United States Patent
Wilson et al.

(10) Patent No.: US 6,399,370 B1
(45) Date of Patent: *Jun. 4, 2002

(54) COMPOSITIONS AND METHODS FOR USE OF DEFENSIN

(75) Inventors: James M. Wilson, Gladwyne; Mitchell Goldman, Wynnewood; Robert Bals, Philadelphia, all of PA (US); Ethan D. Stolzenberg, Rockville, MD (US); Mark Anderson, Norristown, PA (US); Michael Zasloff, Merion, PA (US); Prasad Kari, Hatfield, PA (US)

(73) Assignees: The Trustees of the University of Pennsylvania, Philadelphia; Magainin Pharmaceuticals, Inc., Plymouth Meeting, both of PA (US)

( * ) Notice: Subject to any disclaimer, the term of this patent is extended or adjusted under 35 U.S.C. 154(b) by 0 days.

(21) Appl. No.: 09/228,302

(22) Filed: Jan. 12, 1999

Related U.S. Application Data

(63) Continuation of application No. 08/915,011, filed on Aug. 20, 1997, now abandoned.
(60) Provisional application No. 60/023,424, filed on Aug. 22, 1996, provisional application No. 60/027,334, filed on Oct. 1, 1996, and provisional application No. 60/038,685, filed on Feb. 18, 1997.

(51) Int. Cl.$^7$ .......................... C07H 21/00; C12N 1/11; C12N 5/10; C12N 15/12
(52) U.S. Cl. ..................... 435/325; 435/243; 435/320.1; 424/93.2; 536/23.4; 536/23.5
(58) Field of Search .......................... 514/44; 424/93.2; 435/320.1, 243, 325; 536/23.1, 23.5

(56) References Cited

U.S. PATENT DOCUMENTS

| | | |
|---|---|---|
| 4,954,487 A | 9/1990 | Cooper et al. |
| 5,240,846 A | 8/1993 | Collins et al. |
| 5,550,109 A | 8/1996 | Schonwetter et al. |
| 5,625,128 A | 4/1997 | Wilson et al. |

FOREIGN PATENT DOCUMENTS

| | | |
|---|---|---|
| WO | WO 94/28938 | 12/1994 |

OTHER PUBLICATIONS

Bensch et al., 1995, FEBS Letters 368:331–335.
Canto et al.: In: Pulmonary Infections and Immunity, H. Chmel et al., Eds., Plenum, New York, 1994, pp. 1–27.
Chirgwin et al., 1979, *Biochemistry* 18:5294–5299.
Collins et al., 1992, *Science* 256:774–779.
Davis, 1993, *In: Cystic Fibrosis*, pp. 193–218, P. B. Davis, Ed., Dekker, New York.
Diamond et al., 1993, Proc. Natl. Acad. Sci. 90:4596–4600.
Diamond et al., 1991, Proc. Batl. Acad. Sci. USA 88:3952–3956.
Diamond et al., 1996, Proc. Natl. Acad. Sci. USA 93:5156–5160.
Eisenhauer et al., 1992, Infect. Immu. 60:3446–3447.
Eisenhauer et al., 1992, Infect. Immu. 60:3556–3565.
Engelhardt et al., 1995, Development 121:2031–2048.
Engelhardt et al., 1993, Human Gene Therapy 4:759–769.
Engelhardt et al., 1992, J. Clin Invest. 90:2598–2607.
Engelhardt et al., 1993, Nature Genet. 4:27–34.
Evans et al., 1994, J. Leuc. Biol. 56:661–665.
Frohman et al., 1988, *Proc. Natl. Acad. Sci. USA* 85:8998–9002.
Ganz et al., 1995, Pharm. Therap. 66:191–205.
Goldman et al., 1997, Cell 88:553–560.
Goldman et al., 1995, Nature Genet. 9:126–131.
Harwig et al., 1994, Meth Enzymol. 236–160–172.
Harwig et al., 1994, FEBS Letters 342:281–285.
Hogan et al., 1986, Manipulating the Mouse Embryo: A Laboratory Manual, Cold Spring Harbor, NY (Too voluminous to submit.
Huttner et al., 1994, Genomics 19:448–453.
Imundo et al., 1995, *Proc. Natl. Acad. Sci. USA* 92:3019–3023.
Jones et al., 1992, J. Biol. Chem. 267:23216–23225.
Joris et al., 1993, *Am. Rev. Respir. Dis* 148:1633–1637.
Kellenberger et al. 1995, *Peptides Res.* 8:321–327.
Konstan et al., 1993, *In: Cystic Fibrosis*, pp. 219–276,, P. B. Davis, Ed, Dekker, New York.
Lehrer et al., 1991, J. Immun. Meth. 137:167–173.
Lehrer et al., 1983, *Infect. Immun.* 42:10–14.
Liu et al., 1996, J. Invest. Med. 44:294A.
Mallow et al., 1996, J. Biol. Chem. 271:4038–4045.
Marchuk et al., 1991, *Nucl. Acids Res.* 19:1154.
McCray et al., 1997, Am. J. Respir. Cell. Mol. Biol. 16:343–349.
Mount, 1982, Nucl. Acids Res. 10:459–472.
Ouellette et al., 1992, FEBS Letters 304:146–148.
Ouellette et al., 1994, Infect. Immu. 62:5040–5047.
Pier et al., 1996, Science, 271:64–67.
Quinton, 1990, *FASEB J.* 4:2709–2717.
Russell et al., 1996, Infect. Immu. 64:1565–1568.
Sambrook et al., 1989, Molecular Cloning, A Laboratory Manual, Cold Spring Harbor, New York (Too voluminous to submit).
Schonwetter et al., 1995, Science 267:1645–1648.
Selsted et al., 1993, J. Biol. Chem. 268:6641–6648.
Smith et al, 1996, Cell 85:229–236.
Steiner et al., 1981, Nature 292:246–248.
Strong et al., 1993, *In: Cystic Fibrosis—Current Topics* Dodge et al., eds., pp. 1–26, Wiley, Chichester.
Tang et al., 1993, J. Biol. Chem. 268:6649–6653.
Zasloff, 1987, *Proc. Natl. Acad. Sci. USA* 84:5449–5453.
Zhang et al., 1996, Am. J. Physiol. 270:C1326–1335.
Zhao et al., 1996, FEBS Letters 396: 319–322.
Zimmermann et al., 1995, Biochemistry 34:13663–13671.

(List continued on next page.)

*Primary Examiner*—Deborah Crouch
*Assistant Examiner*—Peter Brunovskis
(74) *Attorney, Agent, or Firm*—Morgan, Lewis & Bockius, LLP

(57) ABSTRACT

The invention relates to mammalian beta defensin and methods of use thereof for treatment of microbial infection.

16 Claims, 22 Drawing Sheets

OTHER PUBLICATIONS

Huttner et al., FEBS Letters 413:45–49.
Liu et al., 1997, Genomics 43:316–320.
Valore et al., 1996, J. Invest. Med. 44:268A.
Wang et. al.; Influence of Cell Polarity on Retrovirus–Mediated Gene Transfer to Differentiated Human Airway Epithelia, 1998, Journal of Virology : 9818–9826.*
Boucher; Status of gene therapy for cystic fibrosis ling disease; 1999, Jornal of Clinical Investigation vol. 103, No. 4:441–445.*
Grubbs et. al.; Inefficient gene transfer by adenovirus vector to cystic fibrosis airway epithelia of mice and humans, 1994, Nature, vol. 371: 802–806.*
Zabner et. al.; Lack of High Affinity Fibor Receptor Activity Explains the Resistance of Ciliated Airway Epithelia to Adenovirus Infection, 1997, J. Clin. Invest. vol. 100No. 5: 1144–1149.*
Zabner et. al.; Cellular and Molecular Barriers to Gene Transfer by a Cationic Lipid, 1995, Journal of Biological Chemistry, vol. 270, No. 32: 18997–19007.*
Marra et al., GenBank Accession Number, AA065510, US National Library of Medicine, Feb. 1997.*
Orkin et al., "Report and recommendations of the panel to assess the NIH investment in research on gene therapy", issued by the US National Institutes fo Health, Dec. 1995.*

* cited by examiner

```
       →BDNT
  1    D   H   Y   N   C   V   S   S   G   G   Q   C   L   Y   S    15
  1    GAY CAT TAY AAY TGY GTC AGC AGT GGA GGG CAA TGT CTC TAT TCT   45

16    A   C   P   I   F   T   K   I   Q   G   T   C   Y   R   G    30
 46    GCC TGC CCG ATC TTT ACC AAA ATT CAA CGC ACC TGT TAC AGA CGG   90

31    K   A   K   C   C   K
 91    AAG GCC AAG TGC TGC AAG TGA GCTGGGAGTGACCAGAAGAAATGACGCAGAA  142

143    GTGAAATGAACTTTTTATAAGCATTCTTTTAATAAGGAAAATTGCTTTGAAGTATAA    201
                              ←UNIP-2

202    AAAAAAAAAAAAAAAA
```

FIG.1

```
                                                                70
       10        20        30        40        50        60     |
AAGCCTCTGTCAGCTCCAAAAGAGCCAGCCTCCAAAAGAGCCAGCCTCTACCCAGTTCCTGAAATCCTGAGTGTTGCCTGCC 140
       80        90       100       110       120       130    |
AGTCGCCATGAGAACTTCCTACCTCTGCTGTTTACTCTCTGCTTACTTTGTCTGAGATGGCCTCAGGTGG
       M  R  T  S  Y  L  L  F  T  L  C  L  L  L  S  E  M  A  S  G  G 210
      150       160       170       180       190       200    |
TAACTTTCTCACAGGCCTTGGCCACAGATCTGATCATTACCATTGCGTCAGCAGTGGAGGGCAATGTCTCTA
 N  F  L  T  G  L  G  H  R  S  D  H  Y  N  C  V  S  S  G  G  Q  C  L  Y 280
      220       230       240       250       260       270    |
TTCTGCCCTGCCGATCTTTACCAAAATTCAAGGCCACCTGTTACAGAGGGAAGGCCAAGTGCTGCAAGTGAGC
 S  A  C  P  I  F  T  K  I  Q  G  T  C  Y  R  G  K  A  K  C  C  K  -

360
      290       300       310       320       330       340    |350
TGAGAGTGACCAGAAGAAATGACGCAGAAGTGAAATGAACTTTTTATAAGCATTCTTTTAATAAAGGAAAAT 370       380       390       400
TGCTTTTGAAGTGTACCTCAAAAAAAAAAAAAAAAAAAAAAAAAAAAAAA                cDNA

FIG.2A
```

```
HBD  -1MRTSYLLLFTLCLLLSEMASGGNFLTGLGHRSDHYNCVSSGGQCLYSACPIFTKIQGTCYRGKAKCC--K
         ——— ———— —  — — — — —    — — ——— — — —— — ——  —
TAP     MRLHHLLLALLFLVLS-ANSG--FTQGVGMPV---SCVRMKGICVPIRCPQSHKQIGTCVGRAVKCCRKK
```

FIG.2B

```
         10         20         30         40         50         60         70
tttcacatcctctctgcactctggacccctggctgccaccactatgaaaactcattacttctctcctggtgatg
                                            M  K  T  H  Y  F  L  L  V  M 80         90        100        110        120        130        140
atatgttttcttttctcccagatggagccaggtgtggcattctcacagtcttggacgaagaacagatcaa
 I  C  F  L  F  S  Q  M  E  P  G  V  G  I  L  T  S  L  G  R  R  T  D  Q 150        160        170        180        190        200        210
tacaaatgccttcaacatggaggattctgtctccgctccagctgcccatctaataccaactacaggaacc
 Y  K  C  L  Q  H  G  G  F  C  L  R  S  S  C  P  S  N  T  K  L  Q  G  T 220        230        240        250        260        270        280
tgtaaaccagataagcccaactgtttgtaagagctgacagtagtttgaagatgagcataaaggacgagcgat
 C  K  P  D  K  P  N  C  C  K  S 290        300        310        320        330        340        350        360
tgtaaccagataagcccaactgtttgtaagagctgacagtagtttgaagatgagcataaaggacgagcgat
ggattgtaaaattagtgtttaataaatgaaatgttttgaagttttattacatcatatcaagataaattt 370        380        390        400        410        420        430
atttctctgtttagaagagcaatttttttaaaagtatttgggcttagaacaagaggtgagaaatccaga 440
acatctgcctgg
```

FIG.12A mBD-1      MKTHYFLLVMICFLFSQMEPGVGILTSLGRRTDQYKCLQHGGFCLRSSCPSNTKLQGTCKPDKPNCCKS hBD-1      MRTSYLLLFTLCLLLSEMASGGNFLTGLGHRSDHYNCVSSGGQCLYSACPIFTKIQGTCYRGKAKCCK

TAP        MRLHHLLLALLFLVLSAW-SGFTQGVG-----NPVSCVRNKGICVPIRCPGSMKQIGTCVGRAVKCCRKK

LAP        MRLHHLLLALLFLVLSAG-SGFT------QGVRNSQSCRRNKGICVPIRCPGSMRQIGTCLGAQVKCCRRK

BNBD-1                                   DFASCHTNGGICLPNRCPGHMIQIGICFRPRVKCCRSW

BNBD-11                                  GPLSCRRNGGVCIPIRCPGPMRQIGTCFGRPVKCCRSW

GAL-1                                    GRKSDCFRKSGFCAFLKCPSLTLISGKCSRFLY-CCKRIW

β-defensin consensus      -----C-----G-C----CP-----G-C-----CC---

FIG.12B

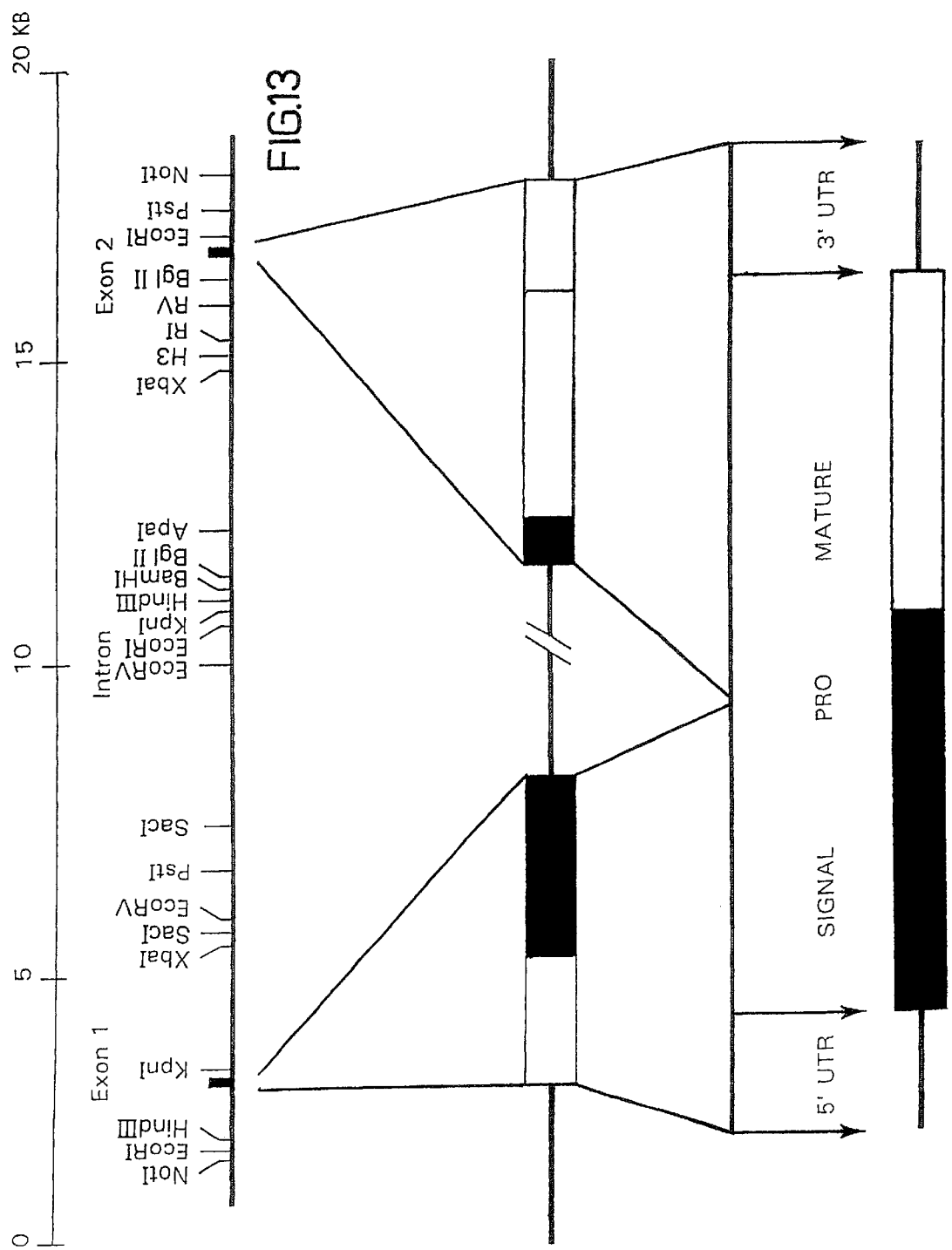

 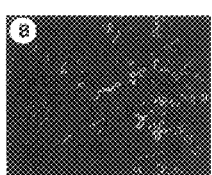  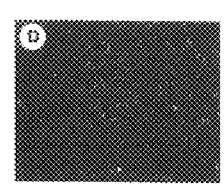
FIG.17A    FIG.17B    FIG.17C    FIG.17D
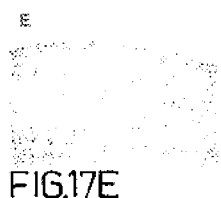 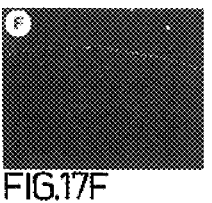 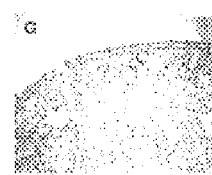 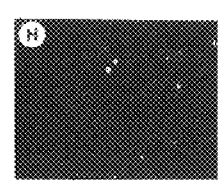
FIG.17E    FIG.17F    FIG.17G    FIG.17H

COMPOSITIONS AND METHODS FOR USE OF DEFENSIN

CROSS REFERENCE TO RELATED APPLICATIONS

This application is a continuation of U.S. application Ser. No. 08/915,011, filed Aug. 20, 1997, now abandoned, which is entitled to priority under 35 U.S.C. §119(e) to Provisional Application Ser. No. 60/023,424, filed on Aug. 22, 1996, Provisional Application Ser. No. 60/027,334, filed on Oct. 1, 1996 and Provisional Application Ser. No. 60/038,685, filed on Feb. 18, 1997.

GOVERNMENT SUPPORT

This invention was supported in part by a grant from the U.S. Government (NIH Grant Nos. P30 DK47757-04 and ROI HL/DK 49040-06) and the U.S. Government may therefore have certain rights in the invention.

FIELD OF THE INVENTION

The field of the invention is antimicrobial therapy for bacterial infection.

BACKGROUND OF THE INVENTION

The respiratory tract of mammals constitutes a barrier between the internal and external milieu. This barrier serves as a first line of defense against invasion by microbial agents. In humans, this defense comprises physical barriers such as mucocillary clearance, biochemical defenses including complement, lysozyme and antibodies, and cells which are capable of generating an inflammatory immune response such as alveolar macrophages (Canto et al.: In: Pulmonary Infections and Immunity, H. Chmel et al., Eds., Plenum, New York, 1994, pp.1–27).

One component of this line of defense is a family of peptides known as defensins. Mammalian defensins are small antimicrobial peptides (3.5–4.5 kDa) that are characterized by the presence of six cysteines which form three disulfide bonds whose ordered array determines whether these proteins are classified as $\alpha$ or $\beta$ defensins. The $\alpha$ defensins are found in granulozytes (Ganz et al., 1995, Pharm. Therap. 66:191–205) and Paneth cells of the small intestine (Jones et al., 1992, J. Biol. Chem. 267:23216–23225; Mallow et al., 1996, J. Biol. Chem. 271:4038–4045) in various species, whereas $\beta$-defensins occur in leucogytes of cattle (Selsted et al., 1993, J. Biol. Chem. 268:6641–6648; Tang et al., 1993, J. Biol. Chem. 268:6649–6653) and fowl (Harwig et al., 1994, FEBS Letters 342:281–285; Evans et al., 1994. J. Leuc. Biol. 56:661–665), where they contribute to host defense system of mucosal surfaces. Lingual and tracheal antimicrobial peptides are $\beta$ defensins expressed in bovine epithelial cells of tongue and trachea (Diamond et al., 1991, Proc. Natl. Acad. Sci. USA 88:3952–3956; Diamond et al., 1993, Proc. Natl. Acad. Sci. USA 90:4596 –4600; Schonwetter et al., 1995, Science 267:1645–1648).

The first $\beta$ defensin isolated from humans, the human $\beta$-defensin 1 (hBD-1), is found in salivary glands, airways, prostate and placenta among other tissues (Bensch et al., 1995, FEBS Letters 368:331–335; Goldman et al., 1997, Cell 88:553–560; McCray et al., 1997, Am. J. Respir. Cell. Mol. Biol. 16: 343–349; Zhao et al., 1996, FEBS Letters 396: 319–322). The expression of mRNA specifying hBD-1 is detected in the colon, small intestine, kidney, prostate, liver and pancreas.

hBD-1 was originally isolated from the hemofiltrate of dialysis patients (Bensch et al., supra). A cDNA sequence specifying only 38 amino acids of mature hBD-1 was identified by Bensch et al. (supra). FIG. 1 illustrates this partial cDNA sequence. The upper line represents the amino acid sequence in single letter code. The primers BDNT and UNIP-2 used for cloning are represented as arrows. The first seventeen nucleotides originate from the degenerate primer BDNT so all possible nucleotides for the third codon position are listed in the sequence (Y=C or T).

Cystic fibrosis (CF) is a multisystem obstructive disease characterized by chronic infection of the airway (Decker et al., 1993, In: Cystic Fibrosis, pp. 193–218, P. B. Davis, Ed., Dekker, New York). The disease is caused by a defect in the cystic fibrosis transmembrane conductance regulator (CFTR), leading to altered $Na^+$ and $Cl^-$ transport and abnormal composition of airway surface fluid (Collins et al., 1992, Science 256:774–779; Joris et al, 1993, Am. Rev. Respir. Dis. 148:1633–1637; Quinton, 1990, FASEB J. 4:2709–2717).

Many hypotheses have been set forth to explain the propensity of the CF airway to become infected (Lehrer et al., 1983, Infect. Immun. 42:10–14; Zasloff, 1987, Proc. Natl. Acad. Sci. USA 84–5449–5453; Konstan et al., 1993, In: Cystic Fibrosis, pp.219–276, P. B. DAVIS, Ed, Dekker, New York; Imundo et al., 1995, Proc. Natl. Acad. Sci. USA 92:3019–3023; Pier et al., 1996, Science 271:64–67). Despite this, the causal chain of events leading from genetic lesions in CFTR to the devastating lung infections suffered by CF patients remains unclear. It has been proposed that dysfunction of airway antimicrobial peptides may be a critical contributing factor to lung infection (Lehrer et al., 1983, supra; Zasloffet al., 1987, supra).

Very recently, antimicrobial activity has been detected in the surface fluid of healthy cultured human airway epithelium (Smith et al., 1996, Cell 85:229–236). Although hBD-1 is widely expressed, antimicrobial activity was absent in the high salt environment of cystic fibrosis epithelium. The activity of a defensin-like molecule returned when the salt concentration was lowered. Cystic fibrosis associated infection may be limited to the respiratory system due to its direct association with the external environment. In addition to the high salt which is the result of defective chloride transport, evaporation of fluid from the airway surface may further concentrate the luminal airway fluid. Both the increase in salt and evaporation of fluid may lower the effects of hBD-1 in CF patients.

There remains a need for antimicrobial therapy directed against bacterial infections in patients having cystic fibrosis and other infectious diseases. There also remains a need for an isolated full length cDNA precursor sequence for hBD-1, that is, a defensin molecule which can be used for the prevention and treatment of infection and for other therapeutic ends. There further remains a need for the development of suitable animal models for the study of the role of defensins in protection against microbial disease and for the discovery of therapeutic agents to combat such disease.

SUMMARY OF THE INVENTION

The invention relates to a cell comprising an isolated nucleic acid encoding human beta defensin-1.

The invention also relates to a cell comprising an isolated nucleic acid encoding rodent beta defensin-1. In one aspect, the rodent defensin is mouse beta defensin-1. In addition, the nucleic acid may further comprises a promotor/regulatory sequence positioned at the 5' end of the human beta defensin-1 or the rodent beta defensin-1.

The invention also includes a vector comprising an isolated nucleic acid encoding human beta defensin-1. In one aspect, the vector may be selected from the group consisting of a plasmid, a virus and a non-viral vector and in another aspect, the vector may be suspended in a pharmaceutical composition. In yet another aspect, the isolated nucleic acid in the vector further comprises a promoter regulatory sequence positioned at the 5' end of the human beta defensin.

There is also included in the invention a vector comprising an isolated nucleic acid encoding rodent beta defensin-1. In one aspect of this aspect of the invention, the defensin is mouse beta defensin-1. In another aspect, the vector is selected from the group consisting of a plasmid, a virus and a non-viral vector, and in yet another aspect, the isolated nucleic acid further comprises a promotor/regulatory sequence positioned at the 5' end of the rodent beta defensin-1.

Also included in the invention is an isolated nucleic acid encoding human beta defensin-1. Preferably, the isolated nucleic acid is cDNA and more preferably, the isolated nucleic acid is the sequence shown in FIG. 2 [SEQ ID NO:3].

In one aspect, the isolated nucleic acid further comprises a promoter/regulatory sequence positioned at the 5' end of the coding region of the human beta defensin-1.

The invention further includes an isolated nucleic acid encoding mouse beta defensin-1. Preferably, the isolated nucleic acid is cDNA. More preferably, the isolated nucleic acid is the sequence shown in FIG. 12 [SEQ ID NO:6].

In one aspect, the isolated nucleic acid may further comprise a promoter/regulatory sequence positioned at the 5' end of the mouse beta defensin-1.

The invention also includes an isolated nucleic acid encoding a saltinsensitive mammalian beta defensin-1. The mammalian beta defensin-1 may be selected from the group consisting of human beta defensin-1 and mouse beta defensin-1 and the isolated nucleic acid may further comprise a promoter/regulatory sequence positioned at the 5' end of the mammalian beta defensin-1.

Also included in the invention is an isolated nucleic acid encoding a mammalian beta defensin-1 having enhanced antimicrobial activity when compared with a wild type mammalian defensin-1 counterpart. In one aspect, the mammalian beta defensin-1 is selected from the group consisting of human beta defensin-1 and mouse beta defensin-1, and in another aspect, the isolated nucleic acid further comprises a promoter/regulatory sequence positioned at the 5' end of the mammalian beta defensin-1.

There is also included in the invention a salt insensitive mammalian beta defensin-1, which may be selected from the group consisting of human beta defensin-1 and mouse beta defensin-1.

In addition, the invention includes a mutated mammalian beta defensin-1 having enhanced antimicrobial activity when compared with a wild type mammalian defensin-1 counterpart. In one aspect of this aspect of the invention, the mutated mammalian beta defensin-1 is selected from the group consisting of human beta defensin-1 and mouse beta defensin-1.

There is also provided in the invention a method of enhancing antimicrobial activity in a tissue sample comprising adding to the sample a mammalian beta defensin-1. In one embodiment, the tissue sample is selected from the group consisting of a mammalian lung tissue sample, a mammalian skin tissue sample and a mammalian blood tissue sample. In another embodiment, the mammalian beta defensin-1 is selected from the group consisting of human beta defensin-1 and mouse beta defensin-1.

In one aspect, the mammalian beta defensin-1 is added to the tissue sample in vivo in a mammal.

In another aspect, the tissue sample is a lung tissue sample and the mammalian beta defensin is human beta defensin-1 which is added to the lung tissue sample by means of a nebulizer or a bronchoscope.

In yet another aspect, the tissue sample is a lung tissue sample and the mammalian beta defensin is human beta defensin-1 which is added to the lung tissue sample in the form of a vector comprising an isolated nucleic acid encoding the human beta defensin-1. When the vector is administered to the human the human beta defensin-1 is expressed therefrom to effect addition of the human beta defensin-1 to the lung tissue sample. In one aspect, the human has a respiratory disease which is preferably emphysema or cystic fibrosis. However, when the respiratory disease is cystic fibrosis, the vector encoding human beta defensin may be salt-insensitive or may have added thereto a compound capable of absorbing salt.

In yet another aspect, the human has a respiratory disease which predisposes the human to pulmonary microbial infection. Preferably, the respiratory disease is emphysema or cystic fibrosis. However, when the respiratory disease is cystic fibrosis, the human beta defensin may be salt-insensitive or may have added thereto a compound capable of absorbing salt.

There is further included in the invention a method of treating a human having a respiratory disease which predisposes the human to pulmonary microbial infection, the method comprising administering to the lungs of the human a pharmaceutical composition comprising human beta defensin-1.

In addition, the invention relates to a method of treating a human having a respiratory disease which predisposes the human to pulmonary microbial infection, the method comprising administering to the lungs of the human a pharmaceutical composition comprising an isolated nucleic acid encoding human beta defensin-1 wherein the human beta defensin-1 is expressed from the isolated nucleic acid in cells of the lungs thereby treating the human.

The invention also includes a method of treating a human having a pulmonary infection, the method comprising administering to the lungs of the human a pharmaceutical composition comprising human beta defensin-1.

There is also provided a method of treating a human having a pulmonary microbial infection, the method comprising administering to the lungs of the human a pharmaceutical composition comprising an isolated nucleic acid encoding human beta defensin-1 wherein the human beta defensin-1 is expressed from the isolated nucleic acid in cells of the lungs thereby treating the human.

In addition, there is provided a method of treating a human having a microbial infection of the skin comprising administering to the skin of the human a composition comprising human beta defensin-1.

Further, there is included a topical composition for administration to the skin of a mammal comprising mammalian beta defensin-1 suspended in a pharmaceutically acceptable carrier. In one aspect, the mammalian beta defensin is selected from the group consisting of human beta defensin-1 and mouse beta defensin-1

Also provided is a pharmaceutical composition comprising human beta defensin-1.

In addition, the invention includes a transgenic mammal comprising an isolated nucleic acid encoding human beta defensin-1.

A method of synthesizing human beta defensin-1 using solid phase 9-Fluorenylmethyloxycarbonyl synthesis is also included. The method comprises regioselective formation of $Cys_5$–$Cys_{34}$, $Cys_{12}$–$Cys_{27}$ and $Cys_{17}$–$Cys_{35}$ by protecting $Cys_5$–$Cys_{34}$ with trityl (triphenylmethyl), protecting $Cys_{12}$ and $Cys_{27}$ with Acm (acetamidomethyl), and protecting $Cys_{17}$ and $Cys_{35}$ with MOL (p-methoxy benzyl).

BRIEF DESCRIPTION OF THE DRAWINGS

FIG. 1 is the prior art amino acid sequence and partial EDNA of hBD-1 [SEQ ID NOS:2 and 1] as described in Bensch et al. (supra).

FIG. 2 depicts the nucleic acid (cDNA) and amino acid sequence of hBD-1. FIG. 2A illustrates the cDNA and deduced amino acid sequence of hBD-1 [SEQ ID NOS:3 and 4, respectively]. Double underline, putative signal sequence; solid underline, mature peptide; dash, termination codon; and, bold underline, polyadenylation signal. FIG. 2B illustrates the putative prepro-peptide sequences of hBD-1 and tracheal antimicrobial peptide (TAP) [SEQ ID NO:5].

FIG. 12 is the cDNA and corresponding amino acid sequence of murine β defensin (mBD-1). FIG. 12A is the cDNA and deduced amino acid sequence of mBD-1 [SEQ ID NOS:6 and 7, respectively]. The first underline indicates the putative mature peptide; the dash represents the termination codon; the second underline indicates the polyadenylation signal. FIG. 12B is a comparison of the putative prepropeptide sequences of mBD-1 [SEQ ID NO:7], hBD-1 [SEQ ID NO:4], tracheal antimicrobial peptide (TAP) [SEQ ID NO:5] and lingual antimicrobial peptide (LAP) [SEQ ID NO:8], all of which were derived from cDNA sequences as well as the peptide sequences of bovine neutrophil β-defensin 1 and 11 (BNBD-1, BNBD-11) [SEQ ID NOS:9 and 10, respectively] and Gallinacin 1 (Gal-1) [SEQ ID NO:11]. The bottom line presents the consensus sequence of β-defensins.

FIG. 13 is a diagram illustrating the structure of the mouse β-defensin 1 gene. A restriction map of the mBD-1 gene together with a schematic drawing of the gene, the cDNA sequence and the predicted structure of the prepropeptide, are shown. The gene is represented schematically as having the following individual components: The 5' untranslated region (5'UTR), open box; signal sequence, shaded box; interrupted prosequence, black box; mature peptide, shaded box; and 3' UTR, open box.

Figures 14A, 14B:
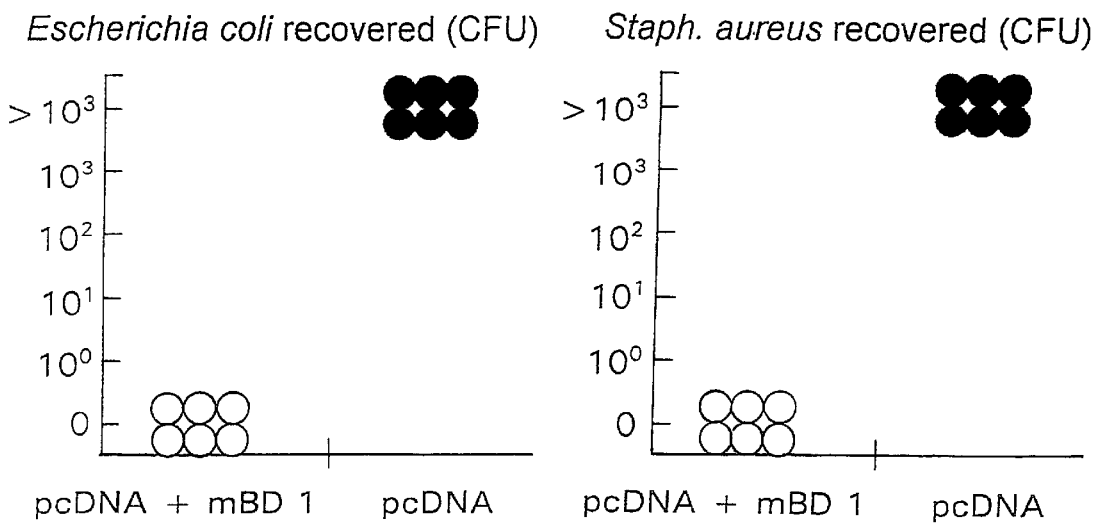
Figure 14C:
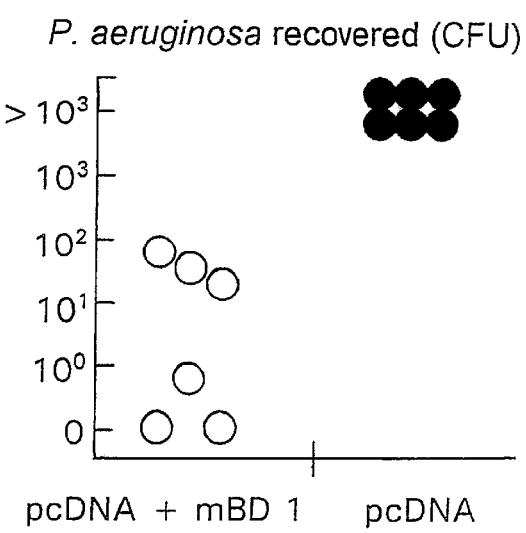
Figure 14D:
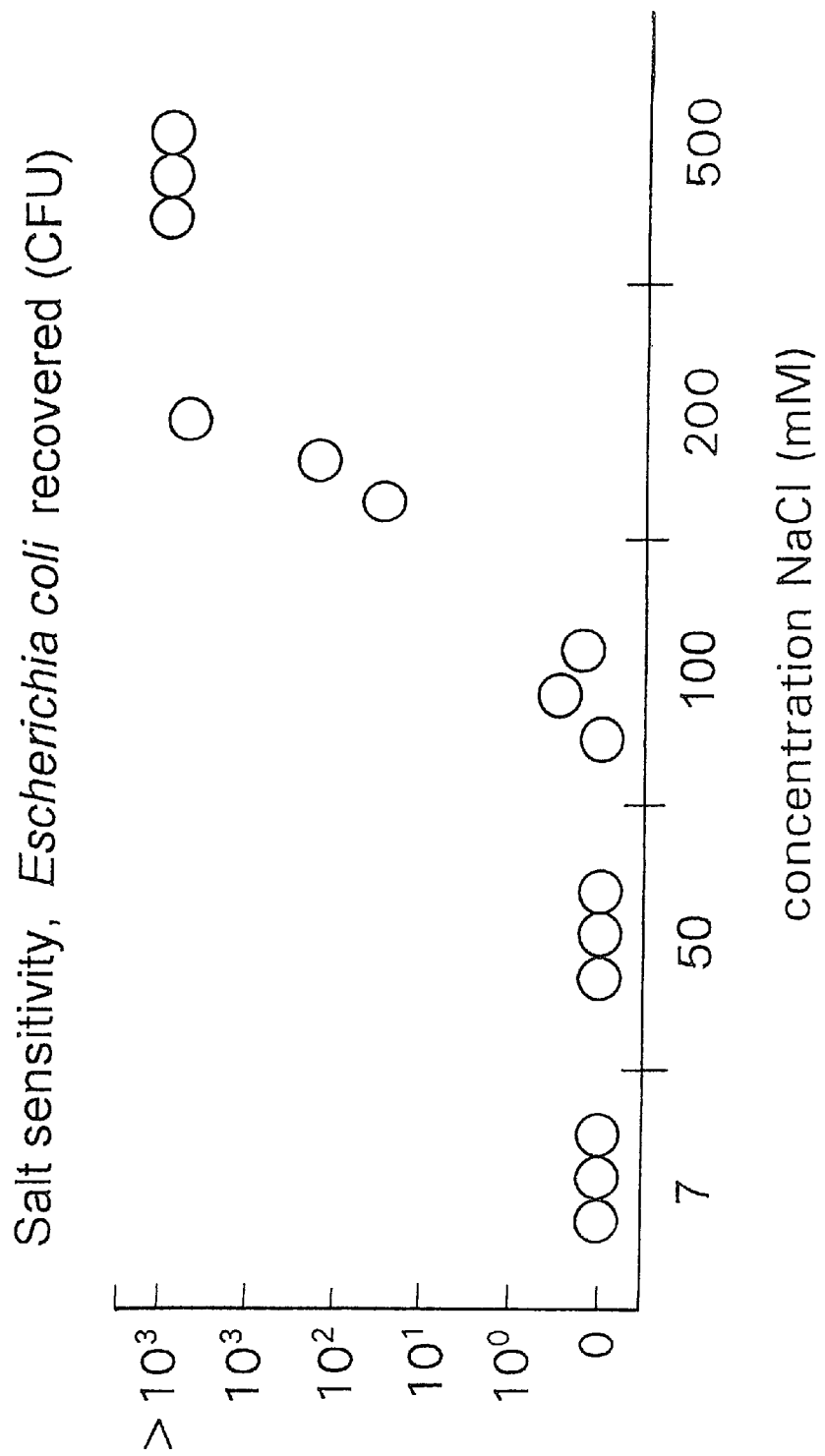

FIG. 14 is a series of graphs depicting the results of antibacterial assays on mBD-1. In FIGS. 14A, 14B and 14C there is shown the results of antibacterial liquid broth coincubation assays. E. coli (FIG. 14A), S. aureus (FIG. 14B) and P. aertiginosa (FIG. 14C) were added at a concentration of $10^3$ to $10^4$ cfu to 50 μl of lysates obtained from cells transfected with vector containing full length mBD-1 cDNA (empty circles) or cells transfected with the vector alone (filled circles). Each circle shown represents the results of an individual transfection experiment. In FIG. 14D there is shown the salt sensitivity of the antimicrobial activity of mBD-1. Extracts of mBD-1 transfected cells were incubated with $5 \times 10^4$ colony-forming units of E. coli D31 in 100 mM phosphate buffer (pH 7.4) and the indicated concentrations of NaCl. After incubation at 37° C. for 1 hour, serial dilutions of bacteria were plated and colonies were counted the following day.

Figure 15A:
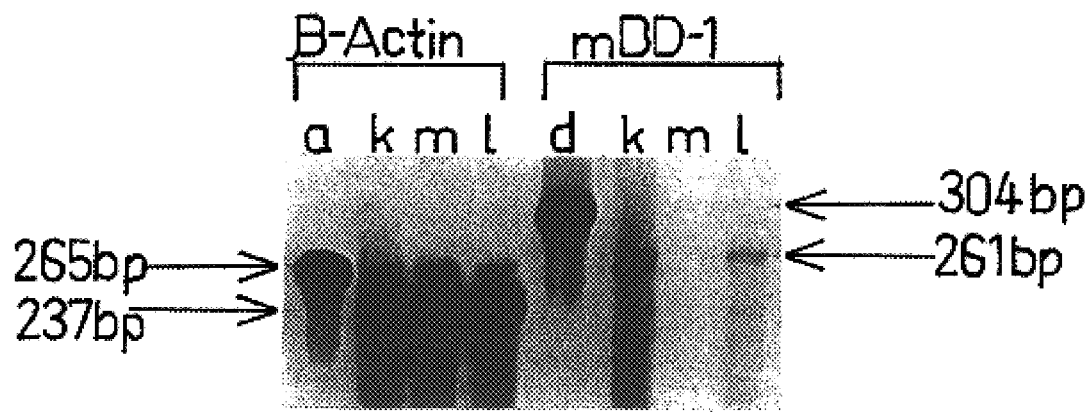
Figure 15B:
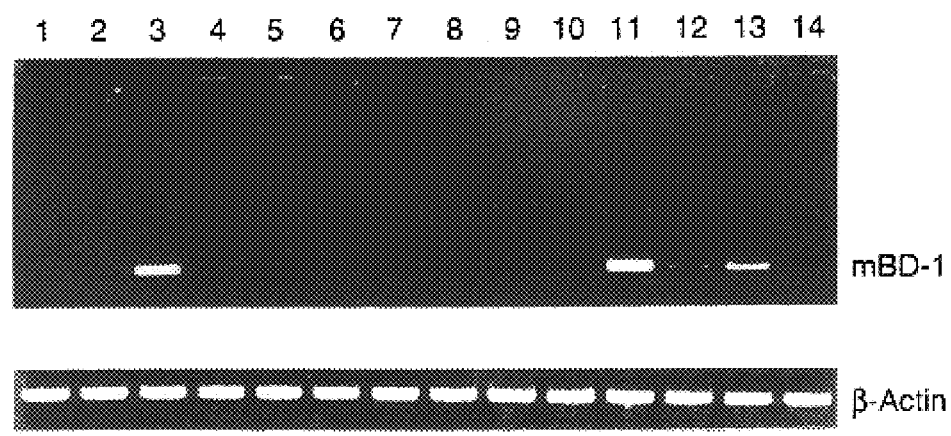

FIG. 15 is a series of images of gels depicting an analysis of mBD-1 expression in RNase protection assays and RT-PCR. FIG. 15A depicts measurement of mBD-1 expression in an RNase protection assay. Total RNA obtained from kidney (k), skeletal muscle (m), and lung/trachea (l) was examined. Hybridization to a labeled riboprobe specific for β-actin (a) or mBD-1 (d) transcripts was performed in separate tubes. FIG. 15B depicts detection of mBD-1 expression in various mouse tissues using nested RT-PCR. PolyA+ RNA was isolated from mouse tissues, reverse transcribed and the cDNAs were amplified using two pairs of mBD-1 specific primers. A single 250 bp band was used as a positive control and was generated during the amplification. The mRNA encoding β-actin was amplified using gene specific primers. 1=trachea, 2=lung, 3 tongue, 4=esophagus, 5=small bowel, 6=large bowel, 7=gall bladder, 8=pancreas, 9=skeletal muscle, 10=heart, 11=fallopian tube, 12=ovary, 13=vagina, and 14=brain.

FIG. 16 is a series of images comprising Panels A-P which illustrate detection of transcripts encoding mBD-1 in the respiratory tract of mice. Antisense (left two columns) and sense (right two columns) probes were used to examine the tissue distribution of mBD-1 transcripts. Representative sections in dark and bright field obtained from nose (Panels A–D), trachea (Panels E–H), large bronchioles (Panels I–L), terminal bronchioles and lung parenchyma (Panels M–P) are shown. The bar in panels A–D represents 0.7 mm, and the bar in panels E–P represents 270 μm.

FIG. 17 is a series of images comprising Panels A–P which depict detection of transcripts encoding mBD-1 in extra pulmonary organs. Antisense (left two columns) and sense (right two columns) probes were used to examine the tissue distribution of mBD-1 transcripts. Representative sections in dark and bright field obtained from kidney (Panels A–D), tongue (Panels E–H), liver (Panels I–L), heart muscle (Panels M–P) are shown. The bar in panels A–H represents 0.7 mm; the bar in panels I–L represents 270 μm; and the bar in panels M–P represents 130 μm.

DETAILED DESCRIPTION OF THE INVENTION

According to the present invention a full length cDNA encoding a human defensin protein has been isolated and characterized. The data provided herein establish that the gene of the present invention, which gene encodes human defensin, is expressed in the human airway. The results of the experiments presented herein further establish that human defensin is an antimicrobial peptide which is highly salt sensitive. These data strongly support a model of CF lung pathology in which elevated NaCl in airway surface fluid compromises defensin activity, leading to infection.

It is believed that the defensin molecule expressed in human airway is inactive in cystic fibrosis leading to the predisposition to infections with pseudomonas and staphylococcus. It is well known that the primary problem in cystic fibrosis lung disease is the chronic colonization of the airway with staphylococcus and pseudomonas, organisms which are not normally associated with respiratory infections in otherwise healthy individuals. This suggests that the primary defect in cystic fibrosis, which is believed to be an abnormal chloride channel, leads to a problem in host defense. The invention thus includes methods and compositions, based on the discovery of the gene encoding human defensin, which provide effective therapies for the treatment of CF.

The human defensin gene (hBD-1) may be obtained by identifying the hBD-1 nucleic acid in a cDNA library using poly A+RNA obtained from cells suspected of expressing defensin. The hBD-1 gene is amplified by 5' and 3' PCR or RACE using nucleic acid probes comprising a signal sequence and a portion of the hBD-1 gene predicted from a partial amino acid sequence of the protein. The details of the isolation of the hBD-1 and mBD-1 genes are provided herein in the experimental example section. However, other equivalent methods of isolation known to those skilled in the art may also be used.

Any other human defensin gene may also be cloned using molecular techniques to isolate defensin DNA from a genomic DNA library or poly A+ RNA obtained from cells expressing defensin. Further, probes derived from the human defensin of the present invention may be generated which comprise conserved nucleotide sequences of defensin genes. These probes may be used to identify additional defensin genes in genomic DNA libraries obtained from other human cells and tissues or from cells and tissues of other mammals using PCR or other recombinant DNA methodology. Such techniques are well known in the art and are described, for example, in Sambrook et al., (1989, Molecular Cloning, A Laboratory Manual, Cold Spring Harbor, New York).

To determine if DNA so selected actually encodes a defensin, the nucleotide sequence of the DNA is obtained. The putative amino acid sequence encoded by the DNA is deduced and this sequence is then compared with the amino acid sequence of a known defensin. Further, the putative defensin gene is cloned into an expression vector, the protein is expressed and is examined for salt sensitive antimicrobial activity as described herein.

Thus, while the gene encoding human defensin has been initially discovered according to the present invention in human bronchial epithelium, a gene encoding a defensin obtained from any other human tissue is also included in the invention. Further, in light of the discovery of a novel mouse β defensin gene as described herein in the present invention, the invention should be construed to include defensin genes from mammals other than humans, which defensin functions in a substantially similar manner to the human defensin described herein. Preferably, the nucleotide sequence comprising the gene encoding defensin is about 50% homologous, more preferably about 70% homologous, even more preferably about 80% homologous and most preferably about 90% homologous to the gene encoding defensin obtained from human bronchial epithelium, i.e., hBD-1.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

Beta defensin molecules and DNAs encoding the same, which are homologous to the beta defensins presented herein should be construed to include a mutants, derivatives and variants of beta defensins.

An "isolated nucleic acid", as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

In other related aspects, the invention includes vectors which contain such isolated nucleic acid and which are preferably capable of directing expression of the protein encoded by the nucleic acid in a vector-containing cell; and cells containing such vectors, either eukaryotic cells or prokaryotic cells, preferably eukaryotic cells.

By the term "vector" as used herein, is meant an autonomously replicating plasmid or a virus. The term should also be construed to include nonplasmid and non-viral compounds which facilitate transfer of nucleic acid into cells, such as, for example, polylysine compounds and the like. Examples of viral vectors include, but are not limited to, adenoviral vectors, adeno-associated virus vectors, retroviral vectors, and the like.

The invention also includes an isolated nucleic acid having a sequence which is in the antisense orientation (i.e., is complementary) to a portion or all of the nucleic acid encoding defensin. By "complementary to a portion or all of a defensin gene" is meant a sequence of nucleic acid which does not encode defensin protein. Rather, the sequence which is being expressed in the cells is identical to the non-coding strand of the defensin gene and thus, does not encode defensin.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both bf the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The invention thus should be construed to include: Nucleic acid encoding defensin and fragments of nucleic acid encoding defensin; and, nucleic acid and fragments of nucleic acid which is in the antisense orientation to nucleic acid encoding defensin.

Fragments of nucleic acid encoding defensin encode portions of defensin which have the biological activity, i.e., which have the antimicrobial activity of defensin as defined herein, or which encode a polypeptide comprising a portion of defensin, which polypeptide is useful, as discussed in detail herein, for the treatment of microbial infections in mammals needing such treatment, such as, but not limited, humans having CF.

The invention also includes an isolated protein encoded by the human defensin gene described herein and other defensin molecules encoded by other defensin genes which may be isolated by the skilled artisan once armed with the present invention. Preferably, the amino acid sequence of a defensin protein so discovered is about 70% homologous, more preferably about 80% homologous, even more preferably about 90% homologous, more preferably, about 95% homologous, and most preferably, at least about 99% homologous to the amino acid sequence of hBD-1.

Substantially pure defensin obtained as described herein may be purified by following known procedures for protein purification, wherein an immunological, enzymatic or other assay is used to monitor purification at each stage in the procedure.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The present invention also provides for analogs of proteins or peptides encoded by a defensin gene. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for biologically active fragments of the polypeptides.

A defensin polypeptide is "biologically active" if it possesses antimicrobial activity as defined herein. As noted above, the antimicrobial activity of wild-type hBD-1 is sensitive to high concentrations of salt. However, the invention also contemplates defensin polypeptides that are either full length or are less than full length, which comprise one or more mutations which render the antimicrobial activity of the defensin insensitive to salt. Thus, mutated defensin polypeptides are biologically active if they possess antimicrobial activity.

As used herein, the term "fragment," as applied to a polypeptide, will ordinarily be at least about fifteen contiguous amino acids, typically at least about twenty five contiguous amino acids, more typically at least about forty contiguous amino acids, usually at least about forty five contiguous amino acids and preferably at least about fifty contiguous amino acids in length.

To identify the region of defensin which confers salt sensitivity on the polypeptide, systematic mutation of the cloned gene may be conducted using ordinary molecular biology techniques. For example, mutant defensin molecules may be generated by linker scanning mutation or other deletion and/or insertion mutation, or a series of stop codons may be introduced in a systematic fashion along the length of the gene. Such technology is well known to the skilled artisan and procedures for practicing the same are described in any molecular biology manual, such as, for an example, Sambrook et al. (supra).

To assess the function of a defensin gene so mutated, the gene may be cloned into an expression vector, and the protein is then expressed in suitable cells. Expression of the gene may be confirmed by performing hybridization designed to detect RNA, such as Northern hybridization or even in situ hybridization. Expression of a defensin polypeptide may be assessed by gel electrophoresis, or by Western blot or any other well known immunological or protein assay.

The antimicrobial activity of defensin so expressed is assessed by obtaining fluid from the cells and determining its effect on the growth of microorganisms, such as staphylococcus or pseudomonas, as described herein. The salt sensitivity of defensin is assessed by including salt in selected samples in the microbial growth assay. Defensin polypeptides having antimicrobial activity that is salt-insensitive are considered to be mutated in a region of defensin which is involved in salt sensitivity. Such mutant DNAs are sequenced and the salt sensitive region of defensin DNA may therefore be defined.

To generate a stable salt-insensitive defensin polypeptide, one or more mutations may be introduced into the region of defensin DNA governing salt sensitivity. Such mutant defensin genes are tested for their ability to give rise to a defensin polypeptide having salt-insensitive antimicrobial activity.

By the term "salt sensitive defensin" as used herein, is meant a defensin molecule which has a lower antimicrobial activity in the presence of a salt concentration which is higher than the physiological concentration of salt, when compared with the antimicrobial activity of the same defensin in the presence of a physiological concentration of salt.

By the term "salt-insensitive defensin" as used herein, is meant a defensin molecule which possesses antimicrobial activity in the presence of a concentration of salt at which the antimicrobial activity of the corresponding wild type defensin is either diminished or ablated.

To determine whether a mutated defensin molecule is salt-insensitive, samples comprising mutated or wild type defensin are assayed for antimicrobial activity in the presence of increasing concentrations of salt. A defensin molecule which possesses antimicrobial activity in the presence of a concentration of salt that diminishes or ablates the antimicrobial activity of wild type defensin is considered to be salt-insensitive.

A defensin gene may also be generated which gives rise to high levels of defensin in a tissue thereby enhancing antimicrobial activity in the tissue.

To express defensin, defensin coding sequences are cloned under the control of a promoter capable of driving high levels of expression of defensin in cells. Many such promoter/regulatory sequences are available in the art including, but not limited to, for example, the human cytomegalovirus immediate early promoter/enhancer sequence, the SV40 early promoter, the Rous sarcoma virus promoter and other retroviral promoter/enhancer sequences.

By the term "promoter/regtilatory sequence" is meant a DNA sequence which is required for expression of a gene fused to the promoter/regulator sequence. In some instances, the promoter/regulatory sequence may function in a tissue specific manner, in that, the promoter/regulatory sequence is only capable of driving gene expression in a cell of a particular tissue type. In some instances, this sequence may be the core promoter sequence and in other instances, this sequence may also include an enhancer sequence and other regulatory elements which are required for expression of the gene in a tissue-specific manner.

Preferably, when the defensin gene further comprises a promoter/regulatory sequence, the promoter/regulatory is positioned at the 5' end of the defensin gene such that it drives expression of the defensin gene in a cell.

By the term "positioned at the 5' end" as used herein, is meant that the promoter/regulatory sequence is covalently bound to the 5' end of the gene whose expression it regulates, at a position sufficiently close to the 5' start site of transcription of the gene so as to drive expression of the gene.

In another aspect, the coding region of defensin is mutated such that the polypeptide encoded thereby has enhanced antimicrobial activity when compared with the corresponding wild type protein expressed by the same animal. Such a wild type protein is referred to herein as a wild type counterpart protein.

A defensin molecule having enhanced antimicrobial activity may also be salt insensitive by simply incorporating a mutation into defensin DNA which renders the protein product salt insensitive along with a mutation which enhances the antimicrobial activity of the molecule.

To generate a defensin polypeptide having enhanced antimicrobial activity, the procedures just described for the introduction of mutations in defensin DNA are followed except that the resulting mutated gene is tested for antimicrobial activity in any quantitative antimicrobial assay. Quantitative microbial assays are well known in the art. In this manner, the region of defensin DNA governing antimicrobial activity may be located and mutations may be introduced therein which provide a defensin molecule having enhanced antimicrobial activity.

As is evident from the experimental data provided herein, the mature human defensin polypeptide exemplified herein is not very large, having thirty six amino acids, the precursor polypeptide having sixty eight amino acids. Thus, it is not necessary that defensin polypeptide be produced solely by cloning and expression. Given its size and the state of the art of polypeptide synthesis, wild type or mutated defensin molecules may be generated by direct synthesis using a peptide synthesizer. Similarly, DNA encoding defensin which is either wild type or comprises one or more mutations but which also has antimicrobial activity may be synthesized in a nucleic acid synthesizer. Thus, the invention should be construed to include synthetic forms of defensin and nucleic acid encoding the same. The invention should also be construed to include analogs of defensin as described above, which analogs may be more soluble or more stable than wild type defensin, and which also contain the above-described mutations rendering defensin salt-insensitive and/ or more antimicrobially active.

By the term "antimicrobial activity" as used herein, is meant the ability to inhibit the growth of or actually kill a population of bacteria. Thus "antimicrobial activity" should be construed to mean both bacteriostatic as well as bacteriocidal activity. Antimicrobial activity should also be construed to include a compound which is which is capable of inhibiting the pathogenesis, i.e., the disease-causing capacity, of a bacterium. Further, an antimicrobial assay for defensin is not necessarily limited by the type of bacteria used in the assay. Typically, the type of bacteria to be used include those bacteria which colonize the respiratory tract in CF patients. For example, the most common infections in the lungs of CF patients are those caused by Staphylococcus and Pseudoinonas species. However, since infections in CF patients are not limited to these bacteria, and moreover, since the defensin molecules of the present invention should not be construed to be limited solely to treatment of infections in CF patients, the antimicrobial assay may include any species of bacteria important in infection of mammals.

Although many antimicrobial assays are known in the art, an example of one such assay is the following. Serial dilutions of fluid obtained from cells transfected with an expression vector comprising a mutated defensin is assayed for antimicrobial activity against a constant number of microbial cells. Controls may include cells transfected with wild type defensin and cells which are transfected with vector sequences in the absence of a functional defensin gene. The level of antimicrobial activity in cell fluid obtained from each set of cells is measured. A mutated defensin gene having enhanced antimicrobial activity is identified by its ability to inhibit the growth of the test organism's at a concentration which is lower than that of the corresponding wild type defensin.

The invention should therefore be construed to include defensin genes and polypeptides which comprise mutations which affect the salt sensitivity and the antimicrobial activity of defensin. Depending upon the location of the salt sensitive region compared with the region of defensin DNA governing antimicrobial activity, salt-insensitive defensin polypeptides which also have enhanced antimicrobial activity may be generated using the procedures described herein in combination with well known molecular biology procedures. Such defensin polypeptides and their corresponding DNAs are also considered to be included in the invention.

Defensin genes and their corresponding peptides are useful for enhancing antimicrobial activity in a tissue sample. Essentially, a defensin protein or a gene encoding defensin is added to the tissue sample, preferably, a lung tissue sample, wherein defensin protein exerts its antimicrobial activity. Defensin is added to the tissue sample either in vitro or in vivo, wherein, when the compound is added to the tissue sample in vivo, it is suspended in a suitable pharmaceutical carrier. When added in vivo, the defensin, or DNA encoding the same, may be added to the tissue sample by way of a nebulizer or a bronchoscope. When the defensin is added in the form of DNA encoding defensin, the DNA may be incorporated into any suitable vector, as described herein, for delivery of the DNA to the tissue sample.

By the term "tissue sample" as used herein, is meant to include both cells which are either in or which surround a tissue and any and all extracellular fluid which is produced by or which surrounds the cells in or around the tissue. The tissue sample may include any mammalian tissue, including, but not limited to, lung tissue, skin tissue, blood tissue (i.e., cells of the blood stream and fluid contained therein), and the like.

In one aspect, the method of the invention includes the addition of hBD-1, or DNA encoding hBD-1, to a lung tissue sample in a human in vivo, wherein the human has a respiratory disease which predisposes the human to pulmonary microbial infection. Such respiratory diseases include, but are not limited to, cystic fibrosis and emphysema, wherein the lungs of the human are compromised such that they are more susceptible to infection by microorganisms than are the lungs of individuals who do not have the respiratory disease. The invention should also be construed to include any other respiratory diseases, such as bronchitis and pneumonia, and any other microbial infection of the lung whether the infection is acute, chronic, transitory, or is the result or is not the result of a predisposing condition.

Defensin genes and their corresponding polypeptides are useful for treatment of a variety of microbial infections in mammals, preferably humans, and more preferably, these molecules are useful for treatment of infections in humans having CF and in animals representing animal models of CF. However, the defensins of the present invention are also useful for treatment of infections in mammals, preferably humans, who are immunosuppressed and are therefore susceptible to acute or chronic infection by bacteria which do not normally infect healthy mammals. For examples, patients that are HIV positive or who are immunosuppressed as a result of treatment for cancer, transplantation procedures, etc., may also benefit from the present invention. Similarly, patients who have other underlying non-CF lung disease such as emphysema, for example, and are therefore susceptible to bacterial infection, may also benefit from the present invention.

In one aspect of the present invention, treatment of infection may involve the administration of a salt sensitive or a salt insensitive defensin to the infected mammal.

Treatment regimes which are contemplated include a single dose or dosage which is administered hourly, daily, weekly or monthly, or yearly. Dosages may vary from 1 $\mu$g to 1000 mg/kg of body weight of defensin, and will be in a form suitable for delivery of the compound to the mammal.

The route of administration may also vary depending upon the disorder to be treated. Defensin is prepared for administration by being suspended or dissolved in a pharmaceutically acceptable carrier such as isotonic saline, isotonic salts solution or other formulations which will be apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema). Preferably, for treatment of patients having lung infection, the route of administration is intranasal delivery by aerosol or via the blood. The appropriate pharmaceutically acceptable carrier will be evident to those skilled in the art and will depend in large part upon the route of administration.

Although wild type defensin may be administered to non-CF patients in any of the pharmaceutical compositions described above, when wild type defensin is administered to a patient having CF, the pharmaceutical composition should comprise a compound capable of absorbing salt in the lung environment for a time sufficient for defensin to act without first being inactivated by the high concentration of salt present. Such compounds will be apparent to those in the art who are now aware of the present invention. The problems associated with the salt sensitivity of defensin may be overcome by using a mutated form of defensin having enhanced antimicrobial activity. Such a molecule, being more potent than its wild type counterpart, may act to inhibit bacterial growth prior to substantial inactivation by salt. However, preferably, when defensin is used to treat a CF patient, a salt-insensitive form is used thus negating inactivation of the antimicrobial activity of defensin by salt.

DNA encoding wild type or mutated defensin may also be used to treat infections in mammals. Examples of methods for the delivery of DNA to mammals are known in the art and are described, for example, in the following references (WO 94 28938 and U.S. Pat. No. 5,240,846), each of which is hereby incorporated herein by reference. DNA may be administered as a naked molecule, it may be encapsulated in a protein or lipid formulation, a synthetic formulation or in any number of viral vectors, such as, for example, adetiovirus, adeno-associated virus, retroviral vectors and the like.

When DNA encoding wild type or mutated defensin is administered to the mammal as described herein, defensin is expressed therein providing therapeutic benefit to the mammal in a manner similar to administration of defensin polypeptide.

Defensin may also be administered to the skin of a mammal for treatment of an infection therein. For administration to skin, defensin may be formulated in any well known skin formulation described, for example, in Remington's Pharmaceutical Science, or in U.S. Pat. No. 4,954,487. Topical administration is useful for treatment of skin infection giving rise to common acne, or for treatment of other microbial infections of skin, such as for example, infection by *Staphylococcus aureus*.

Mammalian homologs of the hBD-1 gene exemplified below may also be identified and isolated once armed with the present invention, Thus, these homologs are included in the present invention. Homologs of the hBD-1 gene may be obtained from any suitable mammal including large mammals such as primates, cows, pigs, and smaller mammals including rabbits and rodents such as rats and mice. Preferably, the invention includes the mouse homolog of hBD-1.

A mammalian homolog of hBD-1 is isolated using hBD-1 probes in combination with PCR or other hybridization technology well known in the art. Mutations in the mammalian homolog may be introduced by following the procedures described herein, which mutations confer salt-insensitivity or enhanced antimicrobial activity on any defensin molecule so isolated.

Transgenic animals may be generated which encode a defensin gene which is incapable of antimicrobial activity. Such animals will be incapable of fighting infections with staphylococcus and pseudomonas and therefore will have a CF phenotype. The animal model is also useful for screening antimicrobials directed against staphylococcus and pseudomonas. Preferably, the transgenic animal is a mouse.

A transgenic mammal encoding a mutated defensin gene which is incapable of antimicrobial activity may be generated as follows. First, the desired mutation is introduced into the defensin gene. Next, the mutated defensin is cloned under the control of a suitable promoter/regulator sequence. The promoter/regulatory sequence used is one which is capable of driving gene expression preferably in airway cells. Examples of such promoter/regulatory sequences include, but are not limited to, those derived from mammalian genes such as β-actin and viruses such as the LTR of retroviruses and the immediate early gene of human cytomegalovirus.

Introduction of the chimeric gene into the fertilized egg of the mammal is accomplished by any number of standard techniques in transgenic technology (Hogan et al., 1986, *Manipulating the Mouse Embryo: A Laboratory Manual*, Cold Spring Harbor, N.Y.). Most commonly, the chimeric gene is introduced into the embryo by way of microinjection.

Once the gene is introduced into the egg, the egg is incubated for a short period of time and is then transferred into a pseudopregnant mammal of the same species from which the egg was obtained (Hogan et al., 1986, *Manipulating the Mouse Embryo: A Laboratory Manual*, Cold Spring Harbor, N.Y.). Typically, about 125 eggs are injected per experiment, approximately two-thirds of which will survive the procedure. About twenty viable eggs are transferred into pseudopregnant animals, four to ten of which will develop into live pups. Typically, about 10–30% of the pups carry the transgene.

Transgenic mammals, preferably mice, which encode mutated defensin may then be assessed for a CF phenotype by examining their ability to handle infection by bacteria, particularly, Staphylococcus and Pseudomonas species. The animals are infected with the subject bacteria and the degree of infection in all tissues is assessed by pathological, histochemical, immunological and other assays well known in the art.

Transgenic animals having a CF phenotype with respect to bacterial infections are useful as animal models for the study of such infections and as models for experimental treatment regimens directed thereto.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The defensin of the present invention is expressed at high levels in epithelial cells of human airway in both CF and non-CF patients. Using transfection assays, the data described in the experimental examples herein establish that expression of human defensin cDNA generates a peptide capable of killing staphylococcus and pseudomonas, which peptide is salt sensitive.

Procedure for cloning hBD-1 cDNA hBD-1 cDNA was amplified from primary human bronchial epithelium poly(A)+ RNA by 5' and 3' RACE (Frohlnan et al., 1988, *Proc. Natl. Acad. Sci. USA* 85:8998–9002). The primer used for 5' RACE was 5'-TTTGGTAAAGATCGGGCA-3' [SEQ ID NO:12], corresponding to CPIFTK [SEQ ID NO:13] of the peptide derived hBD-1 nucleotide sequence (Bensch et al., 1995, FEBS Letters 368:331–335). The primer used for 3' RACE was 5'-ATGAGAACTTCCTACCTT-3' {SEQ ID NO:14], corresponding to signal sequence residues MRTSYL [SEQ ID NO:15]. A two phase procedure was used. To use the. RACE protocol, a short stretch of sequence from an exon is required. In the present invention, the full length cDNA was cloned from cultured human bronchoepithelium primary cell mRNA. From this region, primers oriented in the 3' and 5' directions were chosen which will produce overlapping cDNA when fully extended.

During the first phase of reverse transcription, the 3' ends were amplified as follows. A mixture of RTC buffer, RNasin, $dT_{17}$ adapter primer and AMV reverse transcriptase was created and stored on ice. RNA was heated in $H_2O$ for 3 minutes at 65° C. and then quenched on ice. RNA was added to the above mixture. The mixture was then incubated first at 42° C. for 1 hour and then 52° C. for 30 minutes, diluted and stored at 4° C. as a "cDNA pool."

During the amplification phase, a PCR cocktail was formed of PCR buffer, DMSO, dNTPs, $H_2O$, adapter primer, gene-specific primer and the cDNA pool of the first phase. This mixture was denatured at 95° C. for 5 minutes and cooled to 72° C. Taq polymerase was added and the solution was overlaid with mineral oil that had been heated at 72° C. for 40 minutes.

PCR conditions were as follows: 95° C. for 5 minutes, followed by 35 cycles of 95° C. for 40 seconds, 58° C. for 2 minutes, and 72° C. for 3 minutes, followed by 72° C. for 15 minutes.

In the second phase, using the protocol described in the first phase, a gene-specific primer 1 was substituted for the $dT_{17}$ adapter. Excess primer was removed by use of a Centricon 100 spin filter. The reverse transcription mixture was diluted with 0.1×TE and centrifuged at 1000×g for 20 minutes. This process was repeated and the retained liquid was collected. Speed Vac centrifugation was used to concentrate the solution to 10 μl. 5×Tailing buffer, 1 mM dATP and Terminal d Transferase were added. The solution was incubated for 5 minutes at 37° C. and 5 minutes at 65° C. The solution was then diluted to 500 μl with TE. The amplification phase of procedure one was then followed adding $dT_{17}$ adapter primer in addition to the adapter primer and gene-specific primer 2. Amplification products were subcloned into Bluescript vector (Marchuk et al., 1991, *Nucl. Acids Res*. 19:1154) and sequenced. Multiple clones were analyzed to verify the nucleotide sequence. hBD-1 cDNA was additionally cloned from colon (Caco-2), and tongue (SCC-25) epithelial cells.

Procedures for performing antibiotic activity and salt dependence assays

Human embryonal kidney cells (293) (ATCC CRL 1573) grown in the absence of antibiotics were transfected with the pCMV mammalian reporter vector (Clontech) containing the full length hBD-1 cDNA. Transfected and control mock transfected cells were harvested at 24 to 48 hours postransfection, pelleted by centrifugation, resuspended in 10 mM phosphate buffer (pH 7.4) and lysed by brief sonication. Cell debris was removed by centrifugation and the resulting supernatant was tested for antibiotic activity. Approximately $10^3$ or $10^4$ bacteria were exposed to cell extracts for 2 hours in 10 mM phosphate buffer (pH 7.4) and cell viability was measured by plating several dilutions and counting colonies the following day.

Essentially, for assays involving Pseudomonas and *Escherichia coli*, approximately $5 \times 10^4$ bacterial cells were exposed to about 50 μg to 500 μg of synthetic hBD-1 in 10 mM phosphate buffer (pH 7.4) in a reaction volume of 100 μl. Samples were incubated at 37° C. for 20 minutes and were then diluted to 1 ml total volume with the corresponding test buffer. A volume of 100 μl of this solution and of two 10-fold serial dilutions thereof, were plated and incubated overnight at 37° C. to facilitate colony formation.

A broth culture assay was also used to assess the antimicrobial activity of hBD-1 directed against *Escherichia coli*. In this instance, $1 \times 10^4$ bacterial cells in 200 μl of 0.25×LB broth were incubated at 37DC in the presence or absence of 500 μg of synthetic hBD-1. After 7 hours, the optical density at 630 nm of the cultures was recorded as a measure of bacterial growth. After subtraction of background due to growth medium, the average optical density of the untreated cultures was 0.127 whereas those containing hBD-1 was 0.004, indicating nearly complete suppression of bacterial growth.

Salt dependence of antibiotic activity was measured essentially as described for α-defensins (Lehrer et al., 1983, supra; Selsted et al., 1984, supra). Briefly, approximately $5 \times 10^4$ bacterial cells were exposed to 50 μg of synthetic hBD-1 in 10 mM phosphate buffer (pH 7.4) containing varying concentrations of NaCl in a reaction volume of 100 μl. Reactions were incubated at 37° C. for 20 minutes and were then diluted to 1 ml total volume with the corresponding test buffer. A volume of 100 μl of this solution and of two 10-fold serial dilutions thereof were plated and incubated overnight at 37° C. to facilitate colony formation.

Procedures for performing Northern blot analysis

Cellular mRNA was prepared by guanidinium isothiocyanate extraction (Chirgwin et al., 1979, *Biochemistry* 18:5294–5299), followed by oligo(dT) selection. Tissue mRNA was purchased from Clontech (Palo Alto, Calif.). Cellular mRNA (3 pg), or tissue mRNA (5 µg) was fractionated by formaldehyde gel electrophoresis, transferred to nylon, and hybridized to $^{32}$P-labeled cDNA probe as follows.

An agarose gel was prepared and samples of the RNA were mixed with a formaldehyde gel-running buffer, formaldehyde and formamide. The samples were then incubated at 65° C. for 15 minutes and were chilled on ice and DEPC-treated formaldehyde gel-loading buffer was added. Samples were loaded on the gel, electrophoresis was performed and blots were prepared using standard procedures (Sambrook et al., 1989, Molecular Cloning: A Laboratory Manual, Cold Spring Harbor, N.Y.).

The RNA blots were prehydridized for 8 to 20 hours at 42° C. Hybridization was performed at 42° C. in 50% formamide, 5×SSC, 5×Denhardt's, 50 mM sodium phosphate, and 250 µg/ml salmon sperm DNA. Wash conditions were 50° C. in 0.1×SSC and 0.1% SDS. The probe corresponded to a fragment spanning nucleotides 80 to 379 of the cDNA. The filters were then exposed to X-ray film to visualize bands of RNA. Filters were stripped and re-probed for human β-actin to confirm the presence of intact RNA.

Cell lines in which expression of RNA was assessed were obtained from the American Type Culture Collection and include Caco-2 (ATCC# HTB 37), SCC-25 (ATCC# CRL 1628), Hs27 (ATCC# CRL 1634), A-204 (ATCC# HTB 82), and SK-N-MC (ATCC# H-M 10).

In situ hybridization procedures

To perform cytochemical analyses, lung tissue and/or the xenografts were explanted, embedded in OCT (Tissue-TCK, miles, Inc.), and cryosectioned. Tissue sections (6 µm) were mounted on slides and fixed in 4% paraformaldehyde in PBS (pH 7.4) for 4 hours. Following fixation, sections were dehydrated through graded concentrations of ethanol. Sections were then desiccated overnight under vacuum and stored at −20° C. The following day, sections were treated with 10 µg/ml proteinase K for 30 minutes at 30° C., rinsed twice in 0.2×SSC for 30 seconds each time, fixed in 4% paraformaldehyde in PBS, rinsed twice in 0.1 M triethanolamine (pH ail 8.0) for 4 minutes each time, incubated in 0.25% acetic anhydride for 10 minutes at room temperature, and then dehydrated through graded concentrations of ethanol. Sections were again dried under vacuum before prehybridization for 4 hours at 54° C. in 10 mM Tris (pH 8.0), 50% formamide, 2.5×Denhardt's, 0.6 M NaCl, 1 mM EDTA (pH 8.0), 0.1% SDS, 500 µg/ml tRNA, and 10 mM dithiothreitol (DTT). RNase control sections were treated with 200 µg/ml RNase A for 1 hr at 37° C. before the prehybridization step. Sections were then hybridized with $5 \times 10^5$ cpm/ml $^{35}$S antisense or sense probes for 16 hours at 54° C.

Probes were synthesized using the Promega in vitro transcription system and $^{35}$S UTP and $^{35}$S CTP as labels. cRNA probes for hBD-1 were generated from the T7 and T3 RNA polymerase promoters of full-length cDNA encoding hBD-1 and were subcloned into a Bluescript vector (Stratagene). Probes for CFTR were synthesized from the T7 and SP6 RNA polymerase promoters of a PCR template derived from the cDNA for CFTR. Following hybridization, slides were washed in 4×SSC for 20 minutes (four changes) at room temperature, RNase (20 µg/ml) for 30 minutes at 37° C., 2×SSC/1 mM DTT at room temperature for 10 minutes (two changes), and finally, three 15 minute washes in 0.5×SSC/1 mM DTT at 54° C. Slides were dehydrated through ethanol and air dried before dipping in photoemulsion (Kodak). Slides were developed and analyzed by bright- and dark-field microscopy using a Microphot-FXA Nikon microscope.

The efficiency of adenovirus-mediated CFTR gene transfer to xenografts was determined by dividing the number of positive signals by the total number of cells present in 20 sections derived from multiple blocks of each treated graft. Expression of hBD-1 was evaluated in xenografts from uninfected samples.

Peptide synthesis procedures hBD-1 was synthesized by the solid phase methodology. The regioselective formation of the three disulfide bridges, $Cys_5$–$Cys_{34}$ (I), $Cys_{12}$–$Cys_{27}$ (II) and $Cys_{17}$–$Cys_{35}$ (III) was carried out following procedures described in Kellenberger et al. (1995, *Peptide Res*. 8:321–327) as modified herein. The disulfide bridges were formed by protection of the disulfide bridges as described below and the peptide so generated was characterized by mass spectral, high performance liquid chromatographic and capillary zone electrophoretic analyses. The details of the procedure for the generation of hBD-1 are as follows.

hBD-1 was prepared by the solid phase method of peptide synthesis using the Fmoc (9-Fluorenylmethyloxycarbonyl) strategy. The three disulfide bridges, $Cys_5$–$Cys_{-34}$(I), $Cys_{12}$–$Cys_{27}$ (II) and $Cys_{17}$–$Cys_{35}$ (III) were regioselectively formed. During the synthesis, the sulfide side chains of $Cys_5$ and $Cys_{34}$ were protected with trityl (triphenylmethyl), those of $Cys_{12}$ and $Cys_{27}$ were protected with Acm (acetamidomethyl), and those of $Cys_{17}$ and $Cys_{35}$ were protected with MOL (p-methoxy benzyl). After the synthesis was completed, the peptide was removed from the resin by trifluoroacetic acid treatment, the partially protected peptide was purified by preparative HPLC and the first disulfide bridge was formed between $Cys_5$ and $Cys_{34}$ by aerial oxidation. The peptide was purified and the second disulfide bridge was formed between $Cys_{12}$ and $Cys_{27}$ by treating with iodine. The peptide was once again purified, and the third disulfide bridge was formed by treating the peptide with trifluoromethane sulfonic acid and trifluoroacetic acid followed by aerial oxidation. hBD-1 thus obtained was further purified by HPLC using standard means and was characterized by mass spectrometry, capillary zone electrophoresis and HPLC.

Recombinant Adenoviruses

The structure, production, and measurement of titer of E1-deleted viruses that express β-galactosidase (CMV promoter in a sub360 backbone) and CFTR (CMV-enhanced β-actin promoter in a d17001 backbone) have been described previously (Engelhardt et al., 1993, Human Gene Therapy 4:759–769). The viruses were titered as previously described (Engelhardt et al., Id.).

Generation of Bronchial Xenografts

Human bronchial tissues were obtained from explanted or donor lungs at the time of lung transplantation, and bronchial xenografts were prepared as previously described (U.S. Pat. No. 5,625,128) Engelhardt et al., 1992, J. Clin. Invest. 90:2598–2607; Goldman et al., 1995, Nature Genet. 9:126–131). Surface epithelial cells were removed by incubating the bronchus in protease 14 (Sigma Chemical Co.), plated in primary culture, and maintained for 5 to 7 days prior to release with trypsin. Donor rat tracheas were harvested from $CO_2$ asphyxiated Fisher 344 rats (200 g), from which the epithelium was denuded by three rounds of freeze thawing. These tracheas were ligated to tubing at both ends after seeding of 2×10⁶ bronchial epithelial cells in 30 μl of hormonally defined growth medium (Cloneiics). Grafts were then implanted subcutaneously in the flanks of male nu/nu BALB/c mice and maintained for three weeks in vivo to allow for maturation of a fully differentiated bronchial epithelium. Virus was instilled into the graft lumen (5×10¹⁰ pfu/ml, 100 μl) and expelled with air 6 hours later. Samples from three CF lungs (ΔF508 homozygotes) and six non-CF lungs were used to generate xenografts for these studies.

Transepithelial Potential Difference Measurements

Xenografts were analyzed for changes in potential difference (PD) in response to perfusion with different solutions before and after gene transfer as described (Goldman et al., supra). In preparation for these measurements, animals were anesthetized with intraperitoneally administered ketamine/xylazine (100 μl, 10% v/v) in phosphate-buffered saline (PBS) (pH 7.4). Agar bridges were prepared by filling 21-gauge butterfly needles and tubing with 1 M KCl in 4% agar. The reference bridge was implanted subcutaneously in the flank of the mouse while the exploring electrode bridge was in contact with a reservoir of buffered solution being delivered at a constant rate of 2 ml/minute by a syringe pump. Each bridge was connected by a calomel half-cell to a voltmeter. Measurements were recorded every 10 seconds by a computer interfaced with the voltmeter. Prior to their use, pairs of agar bridges were kept in a common reservoir of buffered solution and only the electrodes that differed by less than 0.2 mV were used for analysis. Each recording measured voltage as a function of time in response to the sequential perfusion of the following: (i) HEPES phosphate-buffered ringers solution (HPBR) containing 10 mM HEPES (pH 7.4), 140 mM NaCl, 5 mM KCl, 1.2 mM MgSO$_4$, 1.2 mM Ca gluconate, 2.4 mM K$_2$HPO$_4$, and 0.4 mM K$_2$HPO$_4$,; (ii) HPBR with 100 μM amiloride; (iii) chloride-free HPBR (gluconate replaces chloride) with 100 μM amiloride; (iv) chloride-free HPBR with 100 μM amiloride, 200 μM 8-cpt cAMP, and 100 μM forskolin; and (v) return to HPBR.

Analyses of ASF from Non-CF and CF Xenografts

To obtain sufficient volumes of ASF for study, airway secretions in xenografts were allowed to accumulate for at least one week and were then collected by expulsion with air. After a brief centrifugation (10⁴×g) to remove the mucus, the supernatant was recovered for antibacterial assays and ion measurements. Sodium and chloride concentrations in ASF were measured using ion-specific glass microelectrodes (Londonderry, NH) calibrated to prepared standards. Antibacterial studies were performed as previously described (Harwig et al., 1994, Meth. Enzymol. 236:160–172; Smith et al, 1996, Cell 85:229–236). Single colonies of bacteria, *P. aeruginosa* (ATCC#39324) or a clinical isolate, were inoculated into LB broth and cultured overnight at 37° C. An aliquot of this culture was transferred to fresh LB and incubated for an additional 2–3 hr at 37° C. to obtain mid-logarithmic-phase cells. The organisms were washed with 10 mM sodium phosphate buffer (pH 7.4), and the concentration of colony-forming units (cfu) per ml⁻¹ was quantitated by measuring its absorbance at 620 nm. ASF (30 ml) was mixed with 1×10³ bacterial cfu and the mixture was incubated for 2 hours at 37° C. Serial dilutions were then plated and colony counts were completed the following day. Analyses of airway surface fluid were conducted from at least 12 individual nor-CF and CF xenografts before and after gene transfer. Identical studies were also performed on six non-CF xenografts treated with a recombinant adenovirus expressing β-galactosidase.

Oligonucleotide Delivery to Xenografts and Molecular Analysis

Phosphorothioate oligonucleotides consisted of 21-mer analogs to the 5' end of the hBD-1 gene. Mismatches are underlined in the sequences given below. Antisense 5'-CAGAAGGTAGGAAGTTCTCAT-3' [SEQ ID NO:16], nonsense 5'-TACAGAGGTGCTCACTGGGTA-3' [SEQ ID NO:17], mismatched 1 5'-CAGAAGGTAGGAAGTTGTCTT-3' [SEQ ID NO:18], and mismatched 2 5'-TCTAAGGTAGGGAGTTCTTTG-3' [SEQ ID NO:19] phosphorothioate oligonucleotides were instilled into non-CF xenografts at a concentration of 20 μM oligonucleotide in 70 μM phosphate buffer (pH 7.4). Any remaining solution was expelled with air the following day. The ability of ASF to kill bacteria was measured before and then three days after oligonucleotide delivery. Antibacterial broth assays were performed as previously described. Grafts were harvested four days after oligonucleotide administration and total RNA was extracted using RNAzol B (Tel-Test, Inc.). RT-PCR was performed on 1 μg of template RNA using the Titan RT-PCR system (Boehringer Mannheim) and primer sets specific for hBD-1 or β1-integrin subunit. Aliquots of the PCR reactions were resolved on a 1% agarose gel, blotted to nitrocellulose, and hybridized to specific ³²P random primer-labeled probes.

Figure 3:
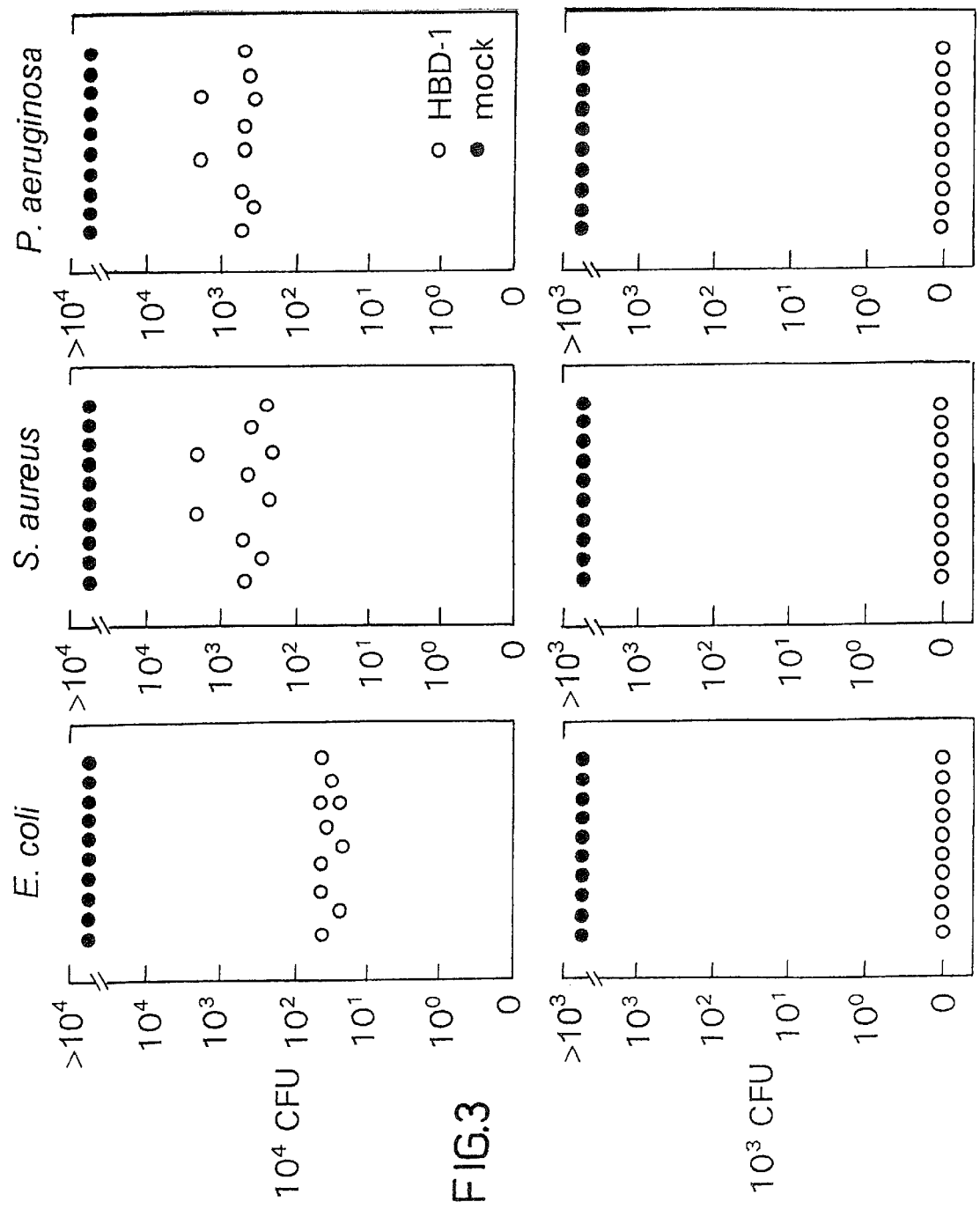
FIG. 3 is a series of graphs depicting the antibiotic activity of extracts derived from human transformed embryonic kidney cells transfected with hBD-1 cDNA. Filled circles represent the results of duplicate antibiotic assays performed on five independent transfected cell extracts; open circles indicate the values obtained in mock transfected cell extracts.

Cloning and characterization of hBD-1 cDNA hBD-1 is a member of the β-defensin family. The protein was originally isolated from the hemofiltrate of dialysis patients (Bensch et al. 1995, supra). According to the present invention, full length hBD-1 cDNA was cloned from mRNA obtained from cultured human bronchoepithelium primary cells. The sequence of the cloned cDNA is shown in FIG. 2A [SEQ ID NO:3]. The cDNA encodes a predicted 68 amino acid precursor that is similar to TAP [SEQ ID NO:5] (FIG. 2B). hBD-1 antibiotic activity was demonstrated by expressing the full length cDNA in transformed human embryonic kidney cells and then testing the antimicrobial activity of extracts of cells so transformed. Extracts from transfected cells exhibited antibiotic activity against *Escherichia coli*, *Pseudomonas aerziginosa*, and *Staphylococcus aureus* whereas those from mock transfected cells did not (FIG. 3).

Cell and tissue expression of hBD-1

Figures 4, 5:
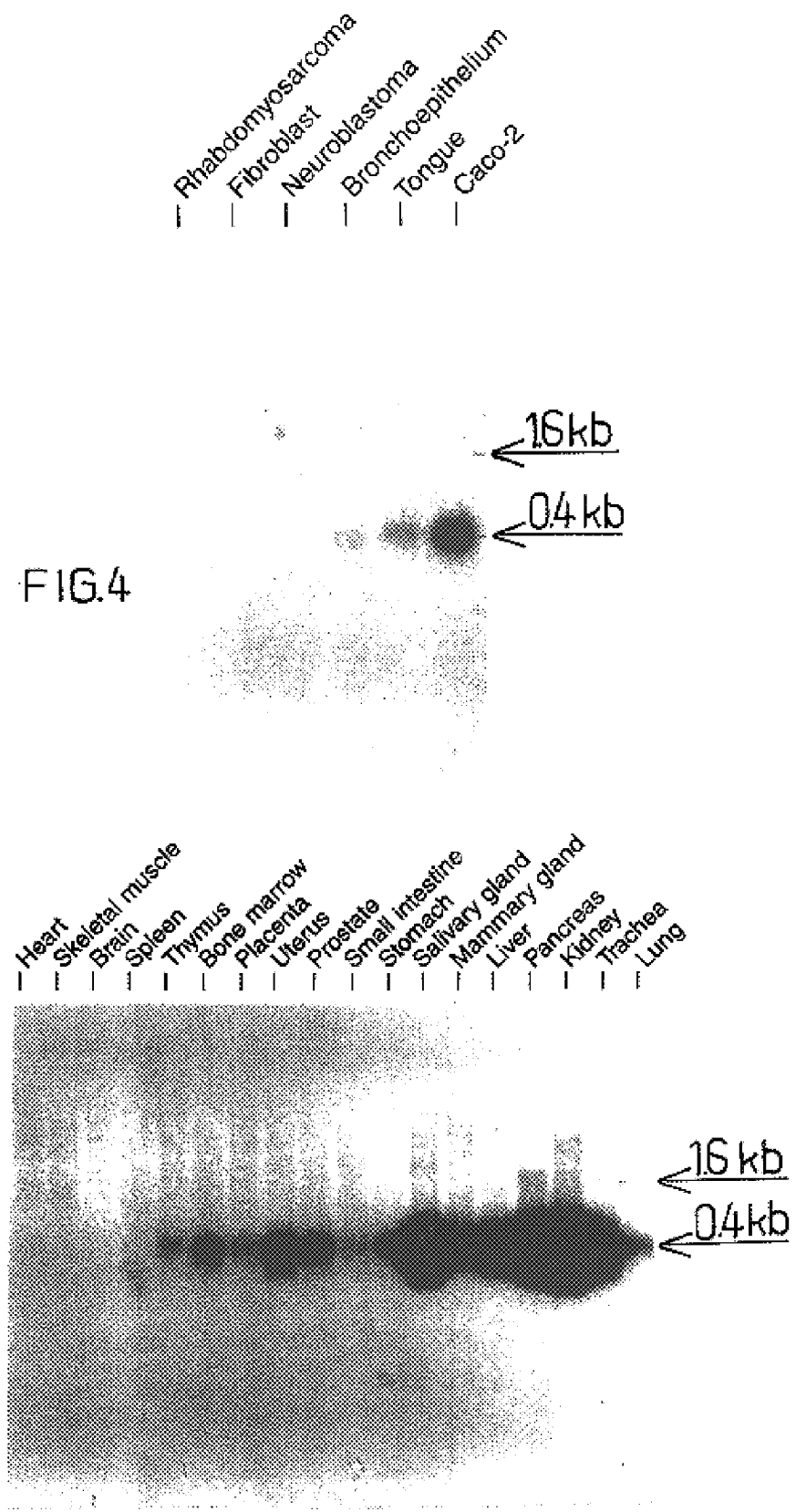
FIG. 4 is a photograph of a gel depicting the distribution of hBD-1 mRNA in epithelial (left three lanes) and non-epithelial (right three lanes) cells.
FIG. 5 is a photograph of a gel depicting the distribution of hBD-1 mRNA in human tissue.
Figure 6A:
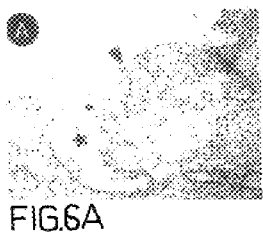
FIG. 6 is a series of images depicting in situ hybridization of a hBD-1 probe to normal and CF pulmonary tissue. Antisense (middle panels) and sense (right panels) oligonucleotides to the gene encoding hBD-1 were hybridized to sections of human lung tissues and were exposed to photoemulsion for six days. Proximal (A-C and G-I) and distal noncartilagenous airways (D-F and J-L) obtained from normal (top rows [A-F]) and CF (middle row [G-L]) lungs are shown. Representative sections obtained from non-CF (M-O) and CF xenografts (P-R) are also shown (bottom rows). Bright-field (left panels) and dark-field (middle panels) photomicrographs of the same region are presented. mRNA encoding hBD-1 was not seen in serial sections hybridized with the antisense probe after treatment of the section with RNase, confirming the specificity of the assay. Arrowheads indicate epithelium; stars denote submucosal glands. Magnification: proximal airway, 8x; distal airway and xenografts, 12.5x.
Figure 6B:
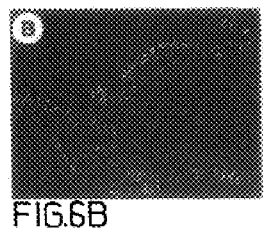
Figure 6C:
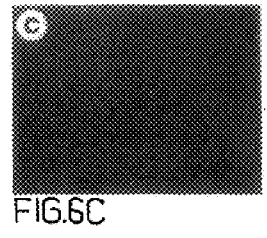
Figure 6D:
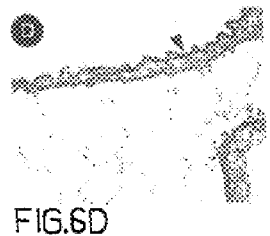
Figure 6E:
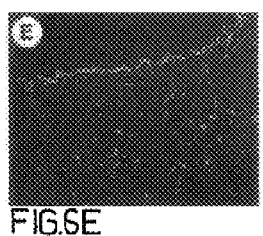
Figure 6F:
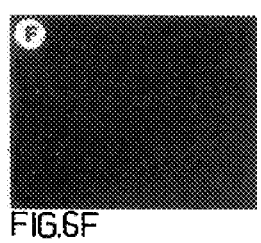
Figure 6G:
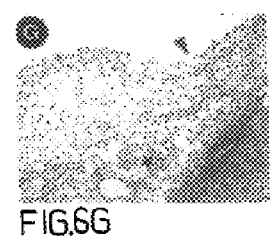
Figure 6H:
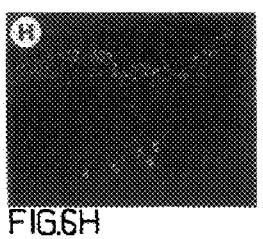
Figure 6I:
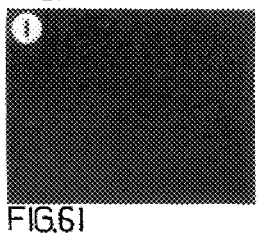
Figure 6J:
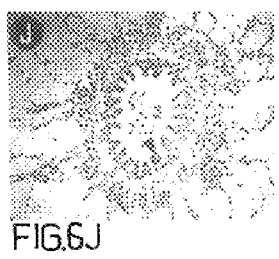
Figure 6K:
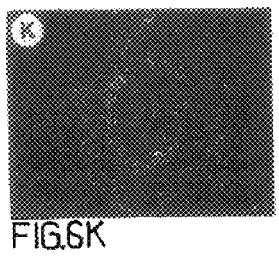
Figure 6L:
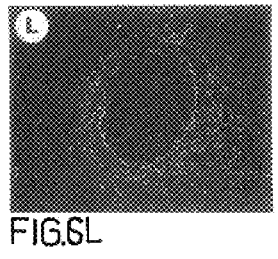
Figure 6M:
Figure 6N:
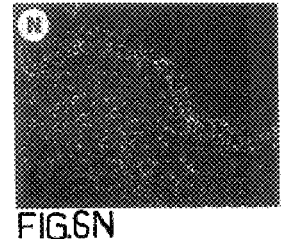
Figure 6O:
Figure 6P:
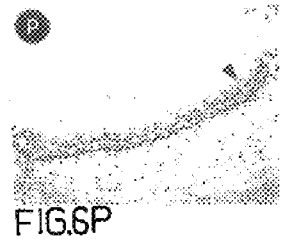
Figure 6Q:
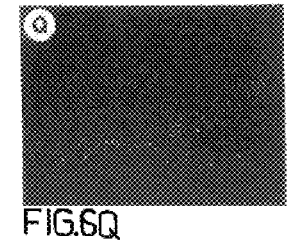
Figure 6R:
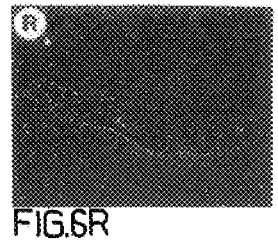

To determine in which human cell types and tissues hBD-1 is expressed, the following experiments were performed. Expression of hBD-1 was first assessed in epithelial cells since it was originally discovered in bronchial epithelial cells (FIG. 4). As is evident from the figure, in addition to primary airway cells, hBD-1 mRNA is expressed in colon (Caco-2) and tongue (SCC-25) epithelial cells. hBD-1 mRNA is absent in several non-epithelial cell types, including human foreskin fibroblasts (Hs68), rhabdomyosarcoma (A-204), and neuroblastoma (SK-N-MC). Sequence analysis of cDNA derived from the epithelial cell lines confirmed the presence of hBD-1.

Northern blot analysis (FIG. 5) reveals expression of hBD-1 at sites with exposed epithelial surfaces and ducts, including colon, small intestine, kidney, prostate, liver, and pancreas. These are all sites associated with CFTR expression and CF pathology (Strong et al, 1993, In: *Cystic Fibrosis—Current Topics* Dodge et al., eds., pp. 1–26, Wiley, Chichester). Such widespread epithelial distribution suggests that hBD-1 may play a general role in mucosal immunity. Additionally, hBD-1 is present in bone marrow (FIG. 5) and in the monocytic cell line U937. hBD-1 is thus produced by cells of both epithelial and hematopoietic origin.

In order to localize expression of hBD-1 mRNA in the respiratory tract, in situ hybridization was performed on human airway tissue. FIG. 6 represents a series of images of non-CF and CF lung tissues hybridized to antisense and sense probes of hBD-1. High level hBD-1 specific RNA was present throughout the superficial conducting airway of non-CF lung from proximal bronchi (FIG. 6, panels A–C) through distal bronchioles (FIG. 6, panels D–F). Expression was also detected throughout the epithelia of submucosal glands (FIG. 6, panels A and B) and alveolar cells (FIG. 6, panels D and E). This differs from the expression of TAP in bovine lung which was primarily detected in proximal airway (Diamond et al., 1991, Proc. Natl. Acad. Sci. USA 93:5156–5160). A similar distribution of hBD-1 expression was demonstrated in the CF lung (proximal airway, FIG. 6, panels G–I; distal airway, FIG. 6, panels J–L). Hybridization of serial sections with the sense probe failed to demonstrate specific signals, confirming the specificity of the assay (FIG. 6, right panels).

Figure 7:
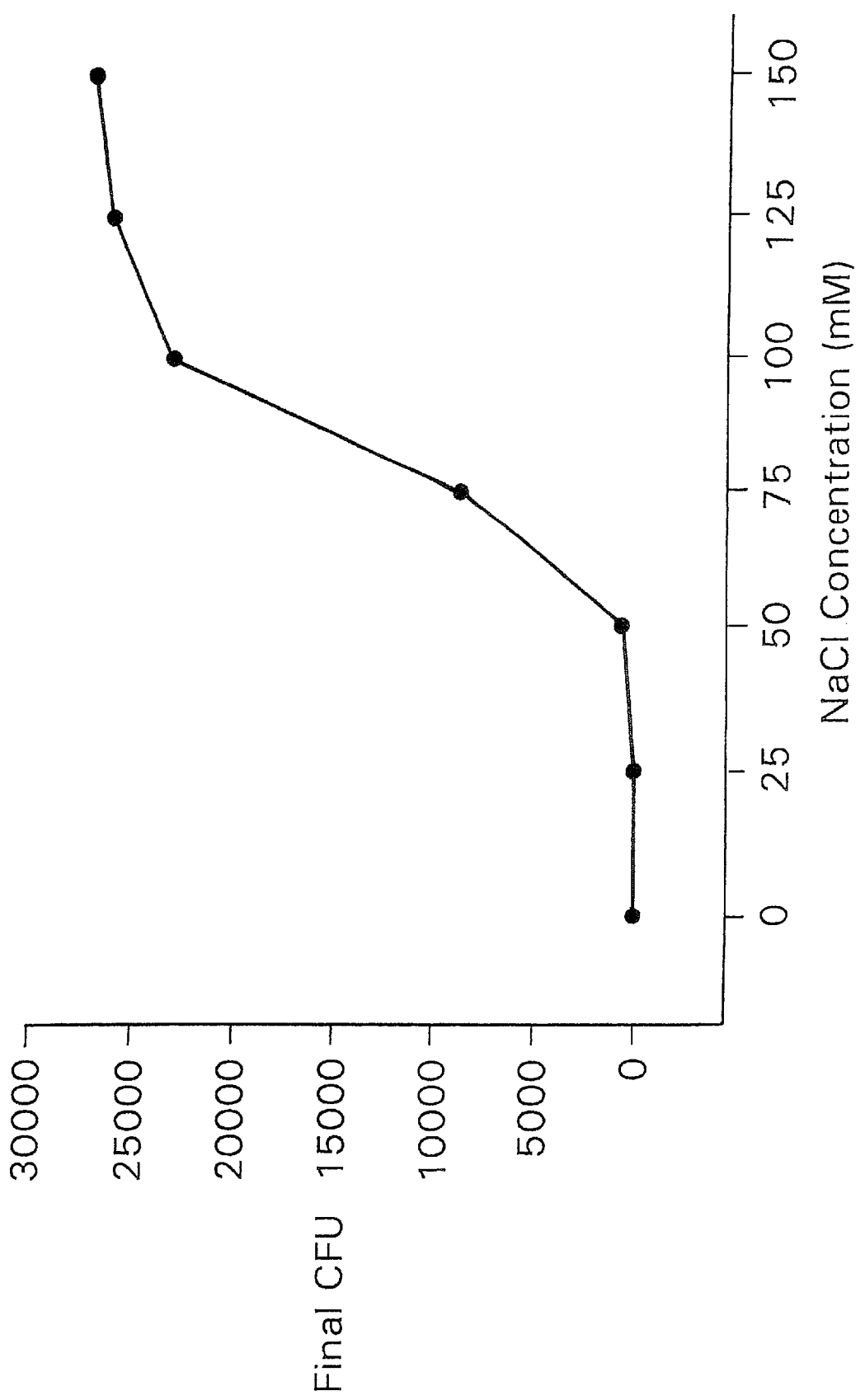
FIG. 7 is a graph depicting salt sensitivity of hBD-1 antimicrobial activity against *Pseudomonas aeruginosa*. Synthetic hBD-1 was incubated with $5\times10^4$ colony forming units of *P. aeruginosa* in 100 µl of 10 mM phosphate buffer (pH 7.4) and the indicated concentrations of NaCl. Reactions were then incubated at 37° C. for 20 minutes. Serial dilutions were plated and colony counts were performed the following day. Similar bacterial killing in low NaCl solution was observed with hBD-1 concentrations ranging from 60 to 500 µg/ml.

To test the hypothesis that hBD-1 is a salt-sensitive antibiotic, a synthetic form of the mature peptide was made which contained the three disulfide bridges (i.e., $Cys_5$–$Cys_{34}$, $Cys_{12}$–$Cys_{27}$, $Cys_{17}$–$Cys_{35}$). In the presence of low NaCl, synthetic hBD-1 exhibited potent bactericidal activity to a broad array of organisms, including *P. aeruginosa* (FIG. 7) and *E. coli*. The impact of NaCl concentration on hBD-1 was evaluated by incubating the synthetic peptide with $5 \times 10^4$ cfu of *P. aeruginosa* in the presence of varying NaCl concentrations (FIG. 7). The antimicrobial activity of hBD-1 exhibited a dramatic salt dependence characterized by a sharp loss of activity as the salt concentration increased from 50 mM to 125 mM. Bacterial killing was observed in low salt with concentrations of hBD-1 varying between 60–500 μg/ml. This titration of hBD-1 activity occurred in the range of NaCl that distinguished non-CF from CF ASF in native human proximal lung and the bronchial xenograft model.

To evaluate further the molecular basis of the defect in bacterial killing in CF ASF, an authentic model for CF lung biology based on the growth of human bronchial xenografts in nu/nu mice was used (Engelhardt et al., 1992, J. Clin. Invest. 90:2598–2607; Engelhardt et al., 1993, Nature Genet. 4:27–34; Goldman et al., 1995, Nature Genet. 9:126–131; Zhang et al., 1996, Am. J. Physiol. 270:C1326–1335). Primary cultures of epithelial cells derived from the proximal airways of CF and non-CF patients were seeded into denuded rat trachea and implanted subcutaneously into nu/nu mice with the proximal and distal ends open to the surface via ligated tubing. Within two weeks, a pseudostratified epithelium of human origin was established. Quantitative morphometric analysis of transmission electron micrographs indicated that the epithelium generated on the xenograft was indistinguishable in organization, cell type distribution, and ultrastructure when compared with the epithelia of the native bronchus from which the epithelial cells were derived (Engelhardt et al., 1992, J. Clin. Invest. 90:2598–2607; Engelhardt et al., 1993, Nature Genet. 4:27–34; Zhang et al., supra). Submucosal glands containing ducts with serous and mucus tubules are partially formed (Engelhardt et al., 1995, Developrnent 121:2031–2048). Previous studies evaluated the ion-conductive properties of the xenograft epithelia through the measurement of surface voltage in response to modulators of ion transport. In these studies, it was established that the functional properties of these epithelia were identical to those observed in the human nasal and intrapulmonary airways (Goldman et al., supra). The most discriminating measurement between non-CF and CF was the change in voltage measured in response to a decrease in luminal Cl and activation with cAMP.

A number of xenografts were established for characterization of the antimicrobial defect in ASF, including 12 grafts obtained from 6 non-CF patients and 12 grafts obtained from 3 CF patients. The results of studies on these xenografts are presented in FIG. 8. Non-CF grafts were distinguished from CF grafts based on the measure of $\Delta v_{96}$ in response to low chloride and cAMP (non-CF: $-14.3 \pm 1.1$ mV; CF: $-0.3 \pm 0.3$ mV). ASF obtained from xenografts was obtained for antimicrobial assays and ion measurements by expelling the luminal contents with air, followed by a brief centrifugation to remove mucus. Direct ionic measurements of non-CF ASF established that the Na and Cl concentrations were $83 \pm 3$ mM. Antimicrobial activity was measured by incubating ASF (30 μl) with $10^3$ *P. aeruginosa* for 2 hours at 37° C. prior to a quantitative assessment of bacterial viability using standard colony counts. ASF obtained from all non-CF xenografts completely killed bacteria. This antibacterial activity was inactivated in high salt and reducing agents, and fractionated through gel filtration with an apparent molecular weight of less than 10. Similar studies performed in CF xenografts revealed a significant increase in Na and Cl content in ASF to $178 \pm 9$ mM and $172 \pm 9$ mM, respectively. ASF obtained from all CF xenografts failed to kill *P. aertiginosa*. Diluting CF ASF in hypotonic solution reconstituted the bactericidal activity.

Figure 8:
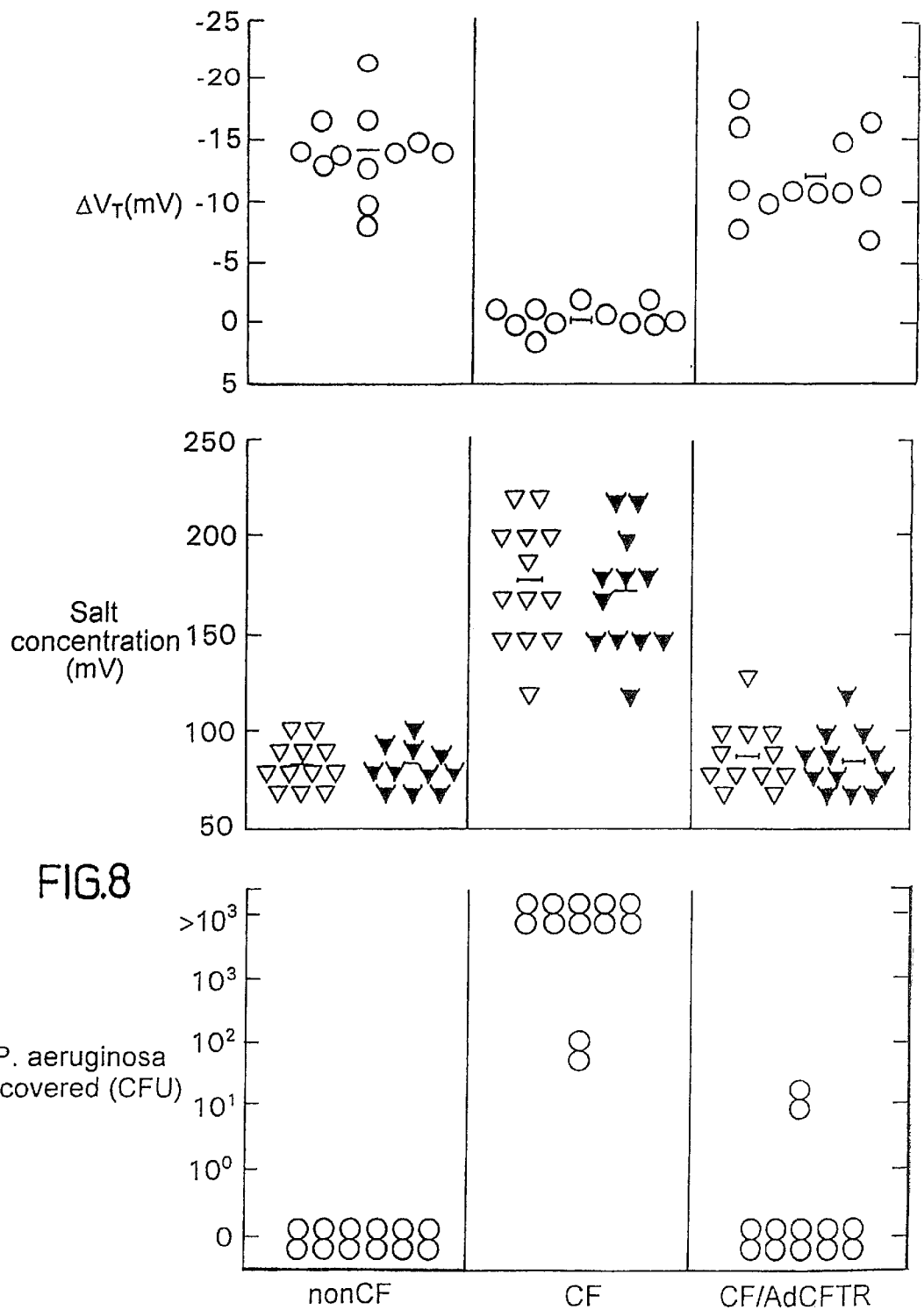
FIG. 8 is a panel of graphs depicting the fact that correction of the CF defect in xenografts normalizes airway surface fluid (ASF) salt concentration and restores its bactericidal activity. ASF was collected from non-CF (left panel), CF (middle panel), and CF bronchial xenografts treated with a recombinant adenovirus expressing CFTR (right panel). In this fluid, sodium (open inverted triangle) and chloride (closed inverted triangle) concentrations were measured and antibacterial liquid broth assays were performed against $10^3$ cfu of *P. aeruginosa* (middle and bottom rows, respectively). Each point shown represents the results obtained from an individual graft (n=12). Transepithelial potential difference measurements were obtained from xenografts both before and after gene transfer. The data presented (top a row) illustrate the change in transepithelial potential difference in amiloride-treated epithelium in response to both chloride substitution and cAMP agonist treatment. As controls, non-CF (n=6) and CF xenografts (n=6) were treated with a recombinant adenovirus expressing β-galactosidase. The ion measurements and antibacterial properties of ASF from grafts treated with the β-galactosidase vector were similar to untreated controls.
Figure 9A:
FIG. 9 is a series of images depicting an analysis of CF xenografts for expression of recombinant mRNA encoding CFTR. Gene transfer to CF bronchial xenografts treated with a recombinant adenovirus expressing CFTR was analyzed by in in situ hybridization. Antisense- (panels B and E) and sense- (panels C and F) probed sections of xenograft tissues were exposed to photoemulsion for one week. Bright-field (panels A and D) and dark-field (panels B and E) images of the same section are shown. The efficiency of gene transfer was determined by dividing the number of positive signals by the total number of cells present in multiple sections from an individual graft. Magnification: (panels A–C) 4x; (panels D–F) 15x.
Figure 9B:
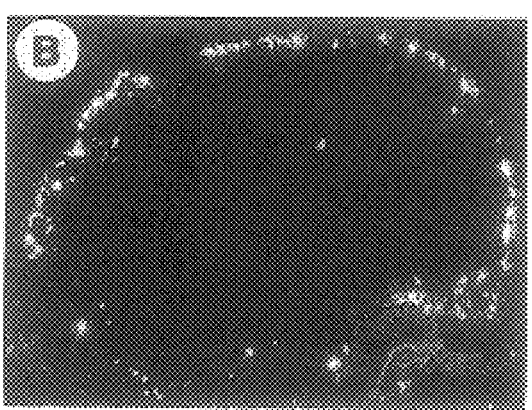
Figure 9C:
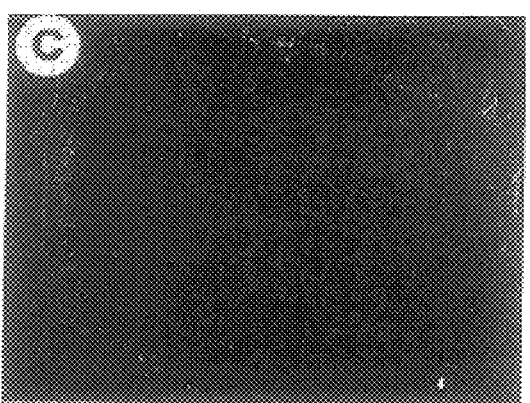
Figure 9D:
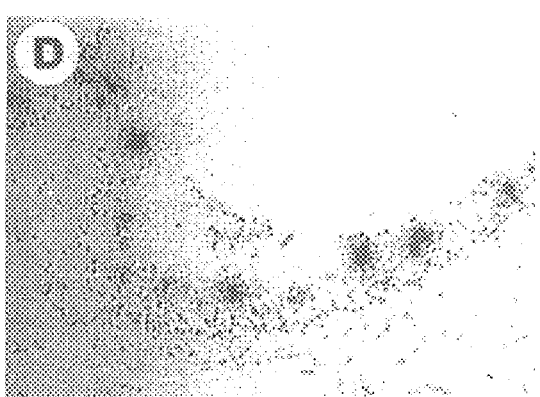
Figure 9E:
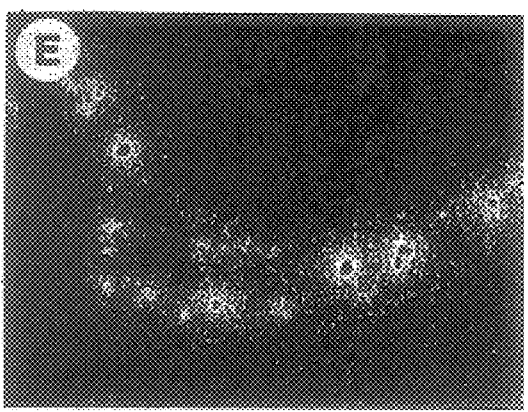
Figure 9F:

The relationship between ionic composition and bactericidal properties of ASF and the epithelial expression of CFTR was further studied in CF xenografts treated with adenoviral vectors containing a cDNA encoding CFTR. El-deleted adenoviral vectors expressing CFTR or β-galactosidase were instilled into the lumen of CF xenografts. In situ hybridization revealed transduction and high-level recombinant CFTR expression in 9%–15% of surface epithelia cells (FIG. 9). CFTR gene transfer corrected the conductive properties of the CF epithelgia ($\Delta v_{96} = -12.7 \pm 0.3$ in response to low chloride and cAMP) and normalized ASF Na ($89 \pm 5$ mM) and Cl ($87 \pm 4$ mM) content (see FIG. 8). ASF from the CFTR-corrected CF xenografts was capable of complete killing of *P. aeruginosa* in 10 out of 12 grafts, with partial killing being observed in the remaining 2 grafts (FIG. 8). CF xenografts treated with similar doses of LacZ virus were indistinguishable from untreated grafts.

Antisense inhibition of hBD-1 in non-CF bronchial xenografts ablates antimicrobial activity in ASF Important to an understanding of CF lung pathogenesis is the identification of the molecule in ASF that confers microbial killing in non-CF lung which is inactive in CF lung. The tissue distribution of hBD-1 expression and its salt-sensitivity to bacterial killing suggested that it is responsible for ASF-mediated host defense. In situ hybridization demonstrated high-level and diffuse hBD-1 expression in epithelia from both non-CF (FIG. 6, panels M–O) and CF (FIG. 6, panels P–R) xenografts that was indistinguishable from native tissue.

Figure 10:
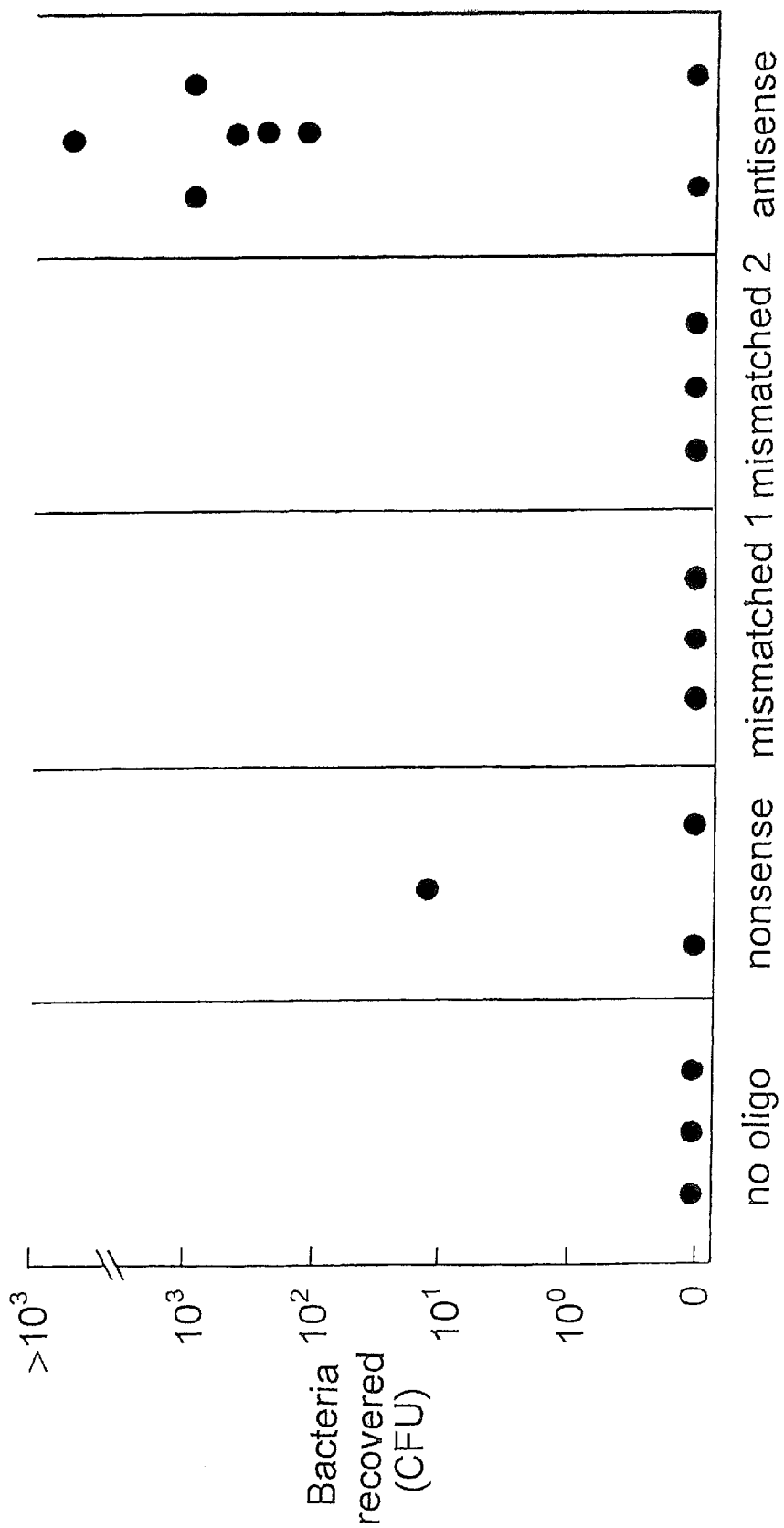
FIG. 10 is a series of graphs depicting down-regulation of hBD-1 RNA by antisense oligonucleotide. Airway surface fluid was collected from non-CF xenografts before and after the instillation of phosphorothioate oligonucleotides. Antibacterial activity was uniformly present in the ASF from all grafts before the administration of any oligonucleotide. Antibacterial broth assays were performed against *P aeruginosa* ($10^3$ cfu) by incubating the organisms with 30 µl of ASF for 2 hr at 37° C., plating serial dilutions of the mixture, and completing colony counts the following day. Each point shown represents the results obtained during examination of an individual graft.
Figure 11:
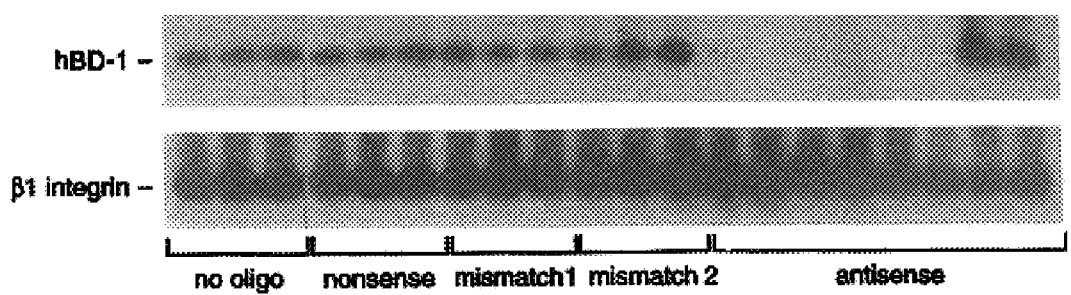
FIG. 11 is a series of images depicting RT-PCR analysis of RNA encoding hBD-1 and β1-integrin subunit from xenografts treated with phosphorothioate oligonucleotides. Four days after the local administration of the oligonucleotide, grafts were explanted and RNA was isolated. RT-PCR was performed using hBD-1 or β-integrin subunit-specific primers, and an aliquot of the reaction mixture was blotted to a nitrocellulose membrane and hybridized with specific probes.

The role of hBD-1 in microbial killing was further studied by genetically ablating its expression using a 21-mer phosphorothioate oligonucleotide antisense DNA specific for the 5' region of mRNA that encodes hBD-1. The controls used in these experiments included a nonsense oligonucleotide containing a scrambled sequence and two mismatched oligonucleotides which were identical to the antisense oligo at 19–21 (mismatch 1) and 14–21 (mismatch 2) nucleotides. The oligonucleotides were instilled into the lumen of non-CF xenografts and three days later, ASF was harvested for microbial killing assays (FIG. 10) prior to removal of the xenografts in order that RNA could be isolated and RT-PCR analysis of hBD-1 expression be performed (FIG. 11). RNA for hBD-1 was detected by RT-PCR at equivalent levels in all non-CF xenografts that were either untreated or preincubated with nonsense, mismatch 1, or mismatch 2 oligonucleotides. Preincubation of non-CF xenografts with these control nucleotides had no effect on the ASF antimicrobial activity; eight out of nine ASF samples completely killed bacteria while one sample yielded only 20 colonies. Preincubation of non-CF xenografts with the hBD-1 antisense oligonucleotide substantially diminished the level of RNA specific for hBD-1 in six out of eight xenografts, each of which failed to completely kill bacteria; full antimicrobial activity was retained in two antisense-treated xenografts that were the same grafts in which the levels of hBD-1 specific RNA were not decreased.

The data presented herein establish that hBD-1 is expressed in the respiratory tract. These data represent the first demonstration of antibiotic peptide expression in human airway epithelium. The causal link between CF dysfunction and repeated infection of the airway in CF patients has never been adequately explained. The data presented herein provide evidence which strongly supports a model in which human airway epithelial defensin activity is impaired by the high salt environment characteristic of the CF airway, leading to compromised host defense and chronic infection. The progressive inhibition of synthetic defensin activity observed in vitro occurs in a range of salt concentrations (50 mM to 100 mM) that is consistent with previously published physiological values of approximately 80 mM $Na^+$ and $Cl^-$ in normal airway surface fluid versus approximately 120 mM in CF airway (Joris et al., 1993, *Am. Rev. Respir. Dis.* 148:1633–1637). The destructive chronic inflammation that is a hallmark of CF lung pathology may represent a compensatory response to the lack of a normal antibiotic shield. Such a model in which salt inhibition of defensin activity leads to CF lung pathology has important therapeutic implications as described herein. The sharp salt sensitivity observed for hBD-1 antimicrobial activity suggests that even relatively modest alterations in ambient ionic strength may enhance or diminish its effectiveness.

Therapies which are designed to alter the salt concentration in CF airway, or which, as described herein, are designed to alter the activity of defensins such as hBD-1, are predicted to greatly alleviate CF symptomology.

Given the data presented herein, it is evident that it would be of great importance to have a suitable animal model, such as mouse or rat, which is available to examine the role of β defensins in pulmonary host defense. Cryotidins, which are expressed in the Paneth cells of the small intestine are the only defensins identified in the mouse (Eisenhauer et al., 1992, Infect. Immu. 60:3556–3565; Ouellette et al., 1992, FEBS Letters 304:146–148; Ouellette et al., 1994, Infect. Immu. 62:5040–5047; Huttner et al., 1994, Genomics 19:448–453) and notably, mouse neutrophils lack defensins (Eisenhauer et al., 1992, Infect. Immu. 60:3446–3447). In the experiments presented below, the isolation and characterization of a murine β defensin, designated mouse β defensin 1 (mBD-1) is described. The experimental procedures used in this study are presented below.

Procedures for cloning of mBD-1 cDNA

The cDNA sequence of human β-defensin 1 (hBD-1) was used to perform a BLAST search at the website of the National Center of Biotechnology Information (NCBI; http://www.ncbi.nlm.nih.gov). A 444 bp EST mouse cDNA sequence submitted by Marra et al. (accession number AA065510) was found which exhibited 51% identity with hBD-1 at the amino acid level including the 6 β defensin specific cysteines.

Reverse-transcriptase polymerase chain reaction (RT-PCR) was used to clone the full length cDNA sequence. Total RNA was isolated from C57BL/6 mouse kidney using Trizol (Gibco BRL) and polyA+ RNA was extracted therefrom using oligodt columns (Qiagen). PolyA+ RNA (approximately 100 ng) was reverse transcribed using Not I-(dT) 18 as primer (First-Strand cDNA Synthesis Kit, Pharmacia Biotech) and 10% of the reaction was used for a PCR reaction. Specific primers to mBD-1 were designed as follows: forward primer (m-def 1)-5'-CGAAGCTTCACATCCTCTCTGCACTCTGG-3' [SEQ ID NO:20] (nucleotides 4–24 of the GenBank sequence plus 9 nucleotides at the 5' - end containing a restriction site for Hind III); reverse primer (m-def 2)-5'-CGACTAGTCCAGGCAGATGTTCTGG-3' [SEQ ID NO:21] (nucleotides 433–444 of the GenBank sequence plus 8 nucleotides at the 5' - end containing a restriction site for Spe I). The PCR products were analyzed on a 1.5% agarose gel and a band of 440 bp was isolated and subdloned into Bluescript II SK⁻-(Stratagene).

Cloning of the mBD-1 genomic sequence

A mouse genomic library constructed in FIX II vector (Stratagene) was screened according to standard procedures (Sambrook et al., supra) using a probe generated by PCR wherein mBD-1 cDNA served as a template gene specific primers (forward: 5'-TTTCACATCCTCTCTGCACT-3' [SEQ ID NO:22] or 5' TGCACTCTGGACCCTGGCT-3' [SEQ ID NO:23]; reverse: 5'-ACCTGGCTCCATCTGGGAGA-3' [SEQ ID NO:24] or 5'-CCATCTGGGAGAAAAGAAAACA-3' [SEQ ID NO:25]). Positive clones were purified and genomic DNA was isolated and suboloned into Bluescript II KS-. The genomic clones were analyzed by partial sequence and digestion with restriction endonucleases.

Testing antimicrobial activity of mBD-1

To test the antibacterial activity of mBD-1, lysates obtained from cells transfected with mBD-1 cDNA positioned in a transfection vector were analyzed. A clinical isolate of *Staphylococcus aureus, Escherichia coli* D31 (Steiner et al., 1981, Nature 292:246–248), and a clinical isolate of *Pseudomonas aeruginosa* were used as test organisms in both diffusion assays and liquid broth assays. To obtain the cell lysates, human adrenal adenocarcinoma cells SW 13 (ATCC. CCL 105) grown in DMEM with 2.5% fetal calf serum in the absence of antibiotics were transfected with pcDNA 3.1-(Invitrogen) containing the fill length mBD-1 cDNA using calcium phosphate (Profection Mammalian Transfection Systems, Promega). As a control, cells transfected with the vector which did not contain the insert were used. Transfected and control mock transfected cells were harvested 48 hours posttransfection, pelleted by centrifugation, resuspended in 500 µl of distilled water and were lysed by brief sonication.

Antibacterial liquid broth assays were performed as previously described for α-defensins (Steiner et al., 1981, Nature 292:246–248). Bacteria ($5 \times 10^4$ cfu) grown in LB broth at mid-log phase were exposed to 50 µl of the cell lysates for 2 hours at 37° C. Cell viability was measured by plating several dilutions and counting colonies the following day. Antibacterial diffusion assays were performed as described by Lehrer et al. (1991, J. Immun. Meth. 137:167–173) with some modification. Essentially, bacteria were grown to mid-log phase in a solution of yeast extract (5 g/l) and tryptone (10 g/l) buffered with 10 mM PIPES at pH 7.5 and $5 \times 10^6$ cfu were diluted in 10 ml of solution additionally containing 1% agarose. After pouring onto 150 mm plates and cooling, cell lysates (5 µl) were pipetted into wells formed with a 4 mm cork corer and allowed to incubate at 30° C. overnight.

To analyze the salt dependency of the activity of mBD-1 against *E. coli* D31, NaCl was added to aliquots of the agarose solution to obtain final concentrations of NaCl of 50 mM, 100 mM, 200 mM and 500 mM. The exact concentration of NaCl in the solutions was measured using Na or Cl sensitive electrodes (Microelectrodes). The pH dependency of mBD-1 activity was studied by adjusting the pH of the agarose solution to 9.0 or 5.5 by adding NaOH or HCl. As a positive control for antibacterial activity, 5 µl of a solution of magainin 1 (1 mg/ml) (Magainin Pharmaceuticals, Inc.) was applied onto agarose plates. Further, liquid broth assays were performed by adding NaCl (final concentrations: 7 mM, 50 mM, 100 mM, 200 mM and 500 mM) to the cell lysates.

Analysis of the expression of mBD-1
Northern blot Analysis

Northern blots of polyA+ RNA (2 µg) obtained from adult mouse tissues (testis, kidney, muscle, liver, lung, spleen, brain, heart) and fetal mice at 7, 11, 15, 17 days of gestation, were purchased from Clontech. $^{32}$P-dCTP random primer labeled cDNA (Rediprime DNA labeling system, Amersham) of mBD-1 cDNA was used as a probe. Hybridization was performed overnight at 42° C. in 50% formamide, 5×SSC, 5×Denhardt's solution, 50 mM sodium phosphate, and 250 µg/ml of salmon sperm DNA. Wash conditions were as follows: 42° C. in 2×SSC/0.1% SDS and finally 65° C. in 0.1×SSC/0.1% SDS. After autoradiography, the filters were stripped and reprobed with a cDNA probe specific for human β-actin.

Ribonuclease protection assay

Ribonuclease protection assays were also used to measure the level of mBD-1 transcripts expressed in lung. Total RNA obtained from lung/trachea, skeletal muscle and kidney were isolated as described above. $^{32}$P-dCTP labeled antisense riboprobes were prepared by in vitro transcription using T7 RNA polymerase promoters in linearized Bluescript KS II—containing mBD-1 (304 bp) or β-actin cDNA (265 bp-SP6/T7 Transcription Kit, Boehringer Mannheim). Hybridizations were performed in separate tubes using 5×10$^5$ cpm of either hBD-1 or β-actin probe and 20 µg of total RNA. RNA-RNA hybrids were digested with RNase A and RNase T1 to yield protected fragments of 261 bp and 237 bp for mBD-1 and β-actin, respectively (Lysate Ribonuclease Protection Kit, Amersham). The results were visualized by electrophoresing the reaction products on a urea-polyacrylamide gel followed by autoradiography.

Reverse transcription PCR

Nested RT-PCR was used to detect low levels of mBD-1 mRNA in several tissues. PolyA+ RNA was isolated from various mouse tissues (trachea, lung, tongue, esophagus, small bowel, large bowel, gall bladder, pancreas, skeletal muscle, heart, fallopian tube, ovary, vagina, brain) and reverse transcribed as described above. The following primers were used in the first round of PCR: forward primer (m-def 5)-5'-TGGACCCTGGCTGCCACCACTATG-3' [SEQ ID NO:26] and reverse primer (m-def 6) 5'-GCTCATTCTTCAAACTACTGTCAG-3' [SEQ ID NO:27]. The products of thig PCR were diluted 1 –50 in distilled water and an aliquot (2 µl) was used as a template for a nested PCR using the same reaction conditions as for the first round and including the following primers: forward primer (m-def 7)-5'-ATGAAAACTCATTACTTTCTCCTGGTGATG-3'[SEQ ID NO:28] and reverse primer (m def 8)-5'-CAATCCATCGCTCGCCTTTTATGCTC-3' [SEQ ID NO:29]. The predicted size of the PCR product was 252 bp. The reverse transcriptase was omitted in the negative control whereas, a RT-PCR with primers specific for mouse β-actin was used as a positive control. The PCR products were analyzed on a 1.5% agarose gel.

In situ hybridization

Various tissues from adult mice (nose, trachea, lung, kidney, liver, tongue, and heart) were harvested from CO$_2$ euthanized animals. The tissues were embedded in OCT (Tissue-TCK, Miles Inc.), and were cryosectioned. Tissue sections of 6 µm thickness were mounted on slides and fixed in 4% paraformaldehyde in PBS (pH 7.4) for 4 hours at 4° C. Following dehydration through graded concentrations of ethanol, sections were desiccated overnight under vacuum and were stored at –20° C. The following day, sections were treated with 10 µg/ml proteinase K for 30 minutes at 30° C., rinsed twice in 0.2×SSC for 30 seconds each time and fixed in 4% paraformaldehyde in PBS. The sections were then rinsed twice in 0.1 M triethanolamine (pH 8.0) for 4 minutes each time, incubated with 0.25% acetic anhydride in 0.1 M triethanolamine for 10 minutes at room temperature, and were then dehydrated through ethanol. Following drying under vacuum, prehybridization was performed for 4 hours at 54° C. in 10 mM Tris (pH 8–0), 50% formamide, 2.5×Denhardt's solution, 0.6 M NaCl, 1 mM EDTA, 0.1% SDS, 500 µg/ml RNA, and 10 mM dithiothreitol. RNase control sections were treated with 200 mg/ml RNase A for 1 hour at 37° C. before the prehybridization step. Sections were then hybridized with 5×10$^6$ cpm/ml of $^{35}$S antisense or sense probes for 16 hours at 54° C. in the prehybridization solution.

Probes were synthesized by in vitro transcription of full length mBD-1 cDNA driven by the T7 or T3 RNA polymerase promoters cloned in Bluegcript KS II—(Promega In Vitro Transcription System). Following prehybridization, slides were washed in 4×SSC for 20 minutes at room temperature, treated with RNase (20 µg/ml) for 30 minutes at 37° C., and washed 2×SSC/1 mM DTT at room temperature for 10 minutes, followed by three washes in 0.5×SSC/1 mM DTT at 54° C. Slides were dehydrated through ethanol and air dried before dipping in photoemulsion (Kodak). Slides were developed and analyzed by bright- and darkfield microscopy using a Microphot-FXA Nikon microscope.

The results of these experiments are now described.

Cloning of the cDNA and the genomic sequence of mBD-1

The EST homologous to the cDNA sequence of hBD-1 was obtained by performing a BLAST search at the website of the National Center of Biotechnology Information (NCBI; http://www.ncbi.nlm.nih.gov) (FIG. 12A) [SEQ ID NO:6]. This cDNA clone exhibited 62% nucleotide identity with the cDNA of hBD-1; the encoded peptide was 51% identical. The murine clone was named mouse β-defensin 1 (mBD-1). The predicted peptide of mBD-1 contained the β-defensin specific conserved amino acids, including the typical array of six cysteines (FIG. 12B). A cDNA clone of mBD-1 was isolated from kidney RNA using RT-PCR. A single product of the predicted size (440 bp) was obtained and cloned into Bluescript II SK. The insert was sequenced and found to be identical to the database clone (FIG. 12A) [SEQ ID NO:6]. The mBD-1 cDNA sequence consists of a 204 bp open reading frame encoding a peptide of 68 amino acids in length with a putative preprosequence (FIGS. 12A and 12B).

A mouse genomic library was screened using PCR-amplified sequences and several positive clones were isolated and further analyzed by hybridization with radiolabeled probes corresponding to the 5' or 3' regions of the mBD-1 cDNA. Two clones contained the total sequence found in the cDNA. A restriction map of the mBD-1 gene is shown in FIG. 13. Comparison of the mBD-1 cDNA and the corresponding genomic clones indicated that the mBD-1 gene contains two exons separated by a 15 kb intron. A TATA box is located in the 5' flanking region and a polyadenylation signal is localized at position 309 of the cDNA. The exon-intron splice site sequences conform to the consensus rule (Mount, 1982, Nucl. Acids Res. 10:459–472). Sequence comparison analysis using a BLAST search at the NCIB identified no additional β-defensin-related sequences in mouse or human DNA, although a cDNA clone (accession number X89820) obtained from rat was found to be 94% identical to the mBD-1 cDNA.

Analysis of antimicrobial activity

To test whether the cloned cDNA sequence encoded an antimicrobial peptide, lysates obtained from cells transfected with the mBD-1 cDNA were used in both diffusion and liquid broth assays and were found to be active against all the bacteria used in both types of assays (FIGS. 14A, 14B and 14C). Lysates obtained from cells transfected with an empty vector failed to demonstrate killing activity supporting the specificity of the assay. These results indicate that mBD-1 possessed antimicrobial activity directed against both gram-positive and gram-negative bacteria. Further, this activity was substantially diminished in the presence of high concentrations of NaCl (FIG. 14D) and in acidic pH.

Expression of mBD-1 in mouse tissues

Hybridization analysis of total cellular RNA revealed the expression of mBD-1 as a transcript of approximately 0.5 kb in the kidney and liver of adult mice. This transcript was not detected by hybridization in other tissues, such as lung, testis, muscle, spleen, brain, heart, or in fetal tissues. RNA obtained from various tissues was also evaluated for the presence of mBD-1 transcripts in the more sensitive ribonuclease protection assay. Using this assay, mBD-1 mRNA was detected in lung/trachea homogenates albeit at much lower levels than that detected in kidney. This assay failed to detect mBD-1 RNA in many other tissues such as muscle (FIG. 15A). A probe specific for to β-actin was used as an internal control.

Nested RT-PCR using mRNA obtained from several mouse tissues was performed to evaluate low level expression of mBD-1. Using this technique, expression of mBD-1 was detected in lung, trachea, tongue, esophagus, fallopian tube, ovary and vagina (FIG. 15B). β-actin was again used as a positive control. No signal was detected when reverse transcriptase was omitted from the reaction.

Figure 16A:
Figure 16B:
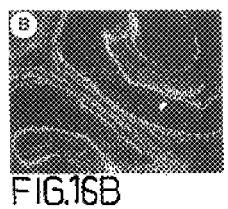
Figure 16C:
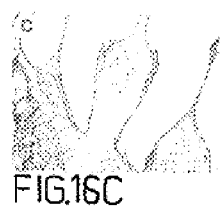
Figure 16D:
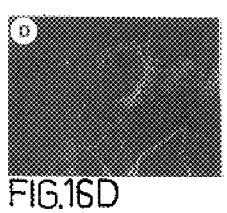
Figure 16E:
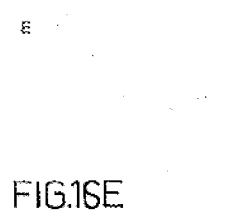
Figure 16F:
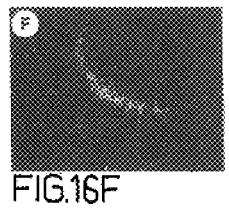
Figure 16G:
Figure 16H:
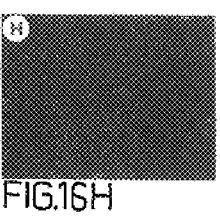
Figure 16I:
Figure 16J:
Figure 16K:
Figure 16L:
Figure 16M:
Figure 16N:
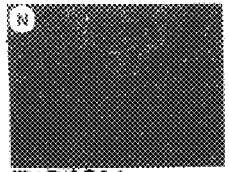
Figure 16O:
Figure 16P:
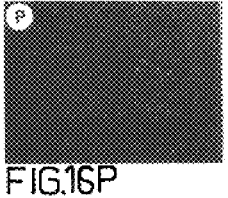
Figure 17I:
Figure 17J:
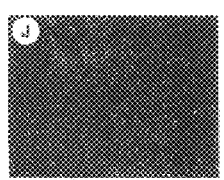
Figure 17K:
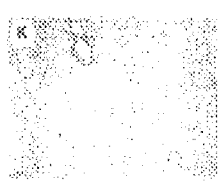
Figure 17L:
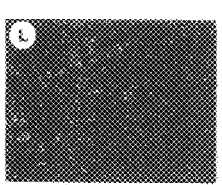
Figure 17M:
Figure 17N:
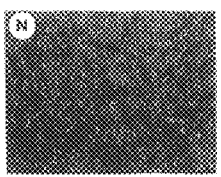
Figure 17O:
Figure 17P:

The tissue distribution of mBD-1 was analyzed at a cellular level by in situ hybridization. mBD-1 transcripts were detected in the epithelia of the nose (FIG. 16A and 16B), the large cartilaginous airways (FIG. 16E and 16F) and the larger bronchioles (FIG. 16I and 16J) when tissue sections were hybridized to the antisense probe specific for mBD-1. A hybridization signal specific for mBD-1 appeared diffusely throughout virtually all the surface epithelial cells of the conducting airway. This, signal was substantially reduced or absent in small bronchioles or lung parenchyma (FIG. 16M and 16N). Positive results were also seen in the distal tubules and collecting ducts of the kidney (FIG. 17A and 17B), the epithelium covering the tongue (FIG. 17E and 17F), and as a diffuse signal in the liver (FIG. 17I and 17J). No signal above that of background levels was detected in the heart muscle (FIG. 17M and 17N). Hybridization using sense mBD-1 riboprobes (FIGS. 16 and 17) or digestion of the tissue with RNase before hybridization to the antisense probe resulted in no detectable signal confirming the sensitivity of the assay.

The cDNA sequence of mBD-1 was discovered in a BLAST search using the nucleotide sequence of hBD-1. Although the similarity of mBD-1 to hBD-1 is only 62%, and 51% at the nucleotide and the amino acid levels, respectively, the amino acid sequence of the putative mBD-1 prepropeptide revealed the structural hallmarks of β-defensins. The amino terminal prepro-portion of the peptide contains several hydrophobic residues, which are characteristic of β-defensins and are found in other β-defensins family members expressed on mucosal surfaces, such as TAP (Diamond et al., 1991, Proc. Natl. Acad. Sci. USA 88:3952–3956; Diamond et al., 1993, Proc. Natl. Acad. Sci. 90:4596 –4600), LAP (Schonwetter et al., 1995, Science 267:1645–1648) or hBD-1 (data presented herein and Bensch et al., 1995, FEBS Letters 368:331–335). The putative mature peptide contains six cysteine residues spaced in a typical array and other conserved amino acids that may have important roles for the conformation and the function of β-defensins, such as G10, P18, G25, and T26 (Zimmermann et al., 1995, Biochemistry 34:13663–13671). Several characteristic charged residues are present in the putative mature peptide.

Analysis of the mBD-1 gene revealed the presence of two exons surrounding a 15 kb intron. The structure of the mBD-1 gene is therefore identical to those of other β-defensins, such as LAP (Diamond et al., 1993, Proc. Natl. Acad. Sci. USA 90:4596–4600) or hBD-1 (Liu et al., 1996, J. Invest. Med. 44:294A) each of which are contained in 2 exons. The first exon contains the pre- and a part of the pro-peptide, whereas the mature peptide and the remaining part of the pro-peptide are encoded by the second exon. These data indicate an evolutionary conservation of the members of the β-defensin group.

Analysis of the cDNA and genomic clones of mBD-1 revealed the presence of typical regulatory elements, such as a TATA box and a polyadenylation signal. However, no binding sites for transcription factors that are involved in the inflammatory response could be found in the mBD-1 regulatory sequence. This region of mBD-1 therefore differs from that of the 5' region of the TAP gene which contains an NF-KB site upstream of the transcriptional start site (Schonwetter et al., 1995, Science 267:1645–1648). Whereas the expression of other mucosal β-defensins, such as LAP and TAP (Diamond et al., 1993, Proc. Natl. Acad. Sci. USA 90:4596 –4600; Schonwetter et al., 1995, Science 267:1645–1648; Diamond et al., 1996, Proc. Natl. Acad. Sci. USA 93:5156–5160; Russell et al., 1996, Infect. Immu. 64:1565–1568), is upregulated by inflammatory mediators and bacterial components, the incubation of cultivated mouse cells (primary mouse tracheal epithelial cells, primary mouse hepatocytes, and mouse lung adenoma cells) with LPS or TNF exhibited no increase in mBD-1 expression. Thus, it appears that mBD-1 may not be regulated by inflammatory responses, but may be part of a constitutively expressed host defense system.

The cloned cDNA sequence specifying mBD-1 encodes an antimicrobial peptide having antimicrobial activity directed against gram-negative and gram-positive bacteria. Further, this activity was lost at high concentrations of salt and in acidic pH. The data presented herein indicate that mBD-1 is expressed in a pattern similar to the. pattern of expression of hBD-1. In the case of mBD-1, the organ in which the most abundant expression was observed was the kidney. However, mBD-1 transcription was also observed throughout the surface epithelia of the conducting airway.

There En appeared to be a gradient of mBD-1 expression throughout the conducting airways wherein the highest expression was noted in proximal structures. This pattern of expression differs from that of hBD-1, which is expressed more uniformly throughout the conducting airways (data presented herein and McCray et al., 1997, Am. J.Respir. Cell. Mol. Biol. 16:343–349). The expression pattern of mBD-1 in airways is of specific importance in light of the data presented herein which establish a salt dependent defect of hBD-1 in the pathogenesis of CF. This model specifically suggests that an elevated concentration of NaCl in airway surface fluid of CF inactivates the antimicrobial activity of defensin and/or other antimicrobial molecules possibly resulting in bacterial colonization and infection. The similar expression patterns of mBD-1 and hBD-1 expression in lung coupled with identical NaCl dependent biological activities demonstrate that the mouse is a useful animal model to investigate the role of antimicrobial peptides in the host defense of the airways.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cell comprising an isolated human beta defensin-1 nucleic acid said nucleic acid consisting of the nucleic acid sequence of SEQ ID NO:3.

2. The cell of claim 1, wherein said nucleic acid further comprises a promoter/regulatory sequence positioned at the 5' end of said human beta defensin-1 nucleic acid.

3. A vector comprising an isolated human beta defensin-1 nucleic acid said nucleic acid consisting of a nucleic acid sequence of SEQ ID NO:3.

4. The vector of claim 3, wherein said vector is selected from the group consisting of a plasmid, a virus and a non-viral vector.

5. The vector of claim 3, suspended in an aqueous solution.

6. The vector of claim 3, wherein said isolated nucleic acid further comprises a promoter/regulatory sequence positioned at the 5' end of said human beta defensin nucleic acid.

7. An isolated human beta defensin-1 nucleic acid said nucleic acid consisting of the nucleic acid sequence of SEQ ID NO:3.

8. The isolated nucleic acid of claim 7, wherein said human beta defensin nucleic acid is cDNA.

9. The isolated nucleic acid of claim 7, further comprising a promoter/regulatory sequence positioned at the 5' end of the coding region of said human beta defensin-1 nucleic acid.

10. An isolated nucleic acid encoding a polypeptide consisting of the amino acid sequence of SEQ ID NO:4.

11. The isolated nucleic acid of claim 10, further comprising a promoter/regulatory sequence positioned at the 5' end of the coding region of said nucleic acid.

12. The isolated nucleic acid of claim 11, wherein the promoter is selected from the group consisting of the human cytomegalovirus immediate early promoter/enhancer sequence, the SV40 early promoter, and the Rous sarcoma virus promoter.

13. The isolated nucleic acid of claim 11, suspended in an aqueous solution.

14. The isolated nucleic acid of claim 12, wherein the isolated nucleic acid is contained in a vector.

15. The isolated nucleic acid of claim 14, wherein the vector is selected from the group consisting of a plasmid, a virus and a non-viral vector.

16. The isolated nucleic acid of claim 14, wherein the vector is suspended in a pharmaceutically acceptable carrier.

* * * * *